United States Patent
Limon et al.

(10) Patent No.: US 10,876,923 B2
(45) Date of Patent: Dec. 29, 2020

(54) APPARATUS, SYSTEM AND METHOD OF DETERMINING ONE OR MORE OPTICAL PARAMETERS OF A LENS

(71) Applicant: 6 OVER 6 VISION LTD., Kfar Saba (IL)

(72) Inventors: Ofer Limon, Kfar Saba (IL); Haim Bachar, Tel Aviv (IL); Nir Altmark, Tel Aviv (IL); Shahar Levy, Rishon LeZion (IL)

(73) Assignee: 6 OVER6 VISION LTD.

( * ) Notice: Subject to any disclaimer, the term of this patent is extended or adjusted under 35 U.S.C. 154(b) by 0 days.

(21) Appl. No.: 16/539,142

(22) Filed: Aug. 13, 2019

(65) Prior Publication Data

US 2019/0368970 A1  Dec. 5, 2019

Related U.S. Application Data

(63) Continuation of application No. 15/572,893, filed as application No. PCT/IB2016/052672 on May 10, 2016, now Pat. No. 10,620,088.

(Continued)

(51) Int. Cl.
*G01B 9/00* (2006.01)
*G01M 11/02* (2006.01)
(Continued)

(52) U.S. Cl.
CPC .......... *G01M 11/0228* (2013.01); *A61B 3/02* (2013.01); *G01M 11/0221* (2013.01);
(Continued)

(58) Field of Classification Search
CPC ............... G03F 7/706; G01M 11/0235; G01M 11/0264; G01M 11/0214; G01M 11/0228
(Continued)

(56) References Cited

U.S. PATENT DOCUMENTS 3,880,525 A   4/1975   Johnson
4,070,115 A   1/1978   Humphrey
(Continued)

FOREIGN PATENT DOCUMENTS

CN   1410747     4/2003
CN   101561347   10/2009
(Continued)

OTHER PUBLICATIONS

Office Action for Chinese Patent Application No. 201680040517.0, dated Nov. 4, 2019, 33 pages (Including 21 pages of English translation).

(Continued)

*Primary Examiner* — Md M Rahman

(74) *Attorney, Agent, or Firm* — Dorsey & Whitney LLP

(57) ABSTRACT

Some demonstrative embodiments include apparatuses, systems and/or methods of determining one or more optical parameters of a lens of eyeglasses. For example, a product may include one or more tangible computer-readable non-transitory storage media including computer-executable instructions operable to, when executed by at least one computer processor, enable the at least one computer processor to implement operations of determining one or more optical parameters of a lens of eyeglasses. The operations may include processing at least one image of an object captured via the lens; and determining the one or more optical parameters of the lens based on the at least one image.

31 Claims, 16 Drawing Sheets

Related U.S. Application Data

(60) Provisional application No. 62/159,295, filed on May 10, 2015, provisional application No. 62/216,757, filed on Sep. 10, 2015, provisional application No. 62/286,331, filed on Jan. 23, 2016.

(51) Int. Cl.
*A61B 3/02* (2006.01)
*G02C 7/02* (2006.01)
*G02C 13/00* (2006.01)
*G06T 7/00* (2017.01)

(52) U.S. Cl.
CPC .... *G01M 11/0235* (2013.01); *G01M 11/0264* (2013.01); *G02C 7/02* (2013.01); *G02C 13/003* (2013.01); *G06T 7/00* (2013.01)

(58) Field of Classification Search
USPC ........................................................ 356/124
See application file for complete search history.

(56) References Cited

U.S. PATENT DOCUMENTS

| | | | |
|---|---|---|---|
| 4,611,913 | A | 9/1986 | Sugino |
| 5,331,394 | A | 7/1994 | Shalon et al. |
| 5,396,324 | A | 3/1995 | Kurachi et al. |
| 5,469,261 | A | 11/1995 | Hellmuth et al. |
| 5,855,074 | A | 1/1999 | Abitbol et al. |
| 5,971,537 | A | 10/1999 | Fukuma et al. |
| 5,973,772 | A | 10/1999 | Fukuma et al. |
| 6,061,123 | A | 5/2000 | Ikezawa et al. |
| 6,349,145 | B1 | 2/2002 | Nakayama et al. |
| 7,646,475 | B2 | 1/2010 | Divo |
| 9,813,693 | B1* | 11/2017 | Baldwin ............ G06T 7/60 |
| 9,835,519 | B2 | 12/2017 | Meng |
| 10,310,269 | B2 | 6/2019 | Decreton et al. |
| 2001/0055111 | A1 | 12/2001 | Yoda et al. |
| 2005/0068495 | A1 | 3/2005 | Jojiki |
| 2005/0190360 | A1 | 9/2005 | Kajino |
| 2006/0152709 | A1 | 7/2006 | Imaizumi |
| 2010/0220285 | A1 | 9/2010 | Simmonds |
| 2013/0016222 | A1* | 1/2013 | Jiang ............ H04N 17/002 348/187 |
| 2013/0155393 | A1 | 6/2013 | Blonde et al. |
| 2014/0300726 | A1 | 10/2014 | Gladnick |
| 2015/0070650 | A1 | 3/2015 | Seriani |
| 2015/0109577 | A1 | 4/2015 | Haddadi et al. |
| 2015/0139534 | A1* | 5/2015 | Komatsu ............ G06T 7/62 382/154 |
| 2015/0330865 | A1 | 11/2015 | Meng |
| 2016/0202498 | A1* | 7/2016 | Ozaki ............ G02C 13/003 351/204 |
| 2016/0299360 | A1* | 10/2016 | Fonte ............ G06Q 30/0621 |
| 2016/0309992 | A1* | 10/2016 | Stith ............ G02B 7/04 |
| 2016/0327779 | A1* | 11/2016 | Hillman ............ G02B 21/367 |
| 2017/0111630 | A1* | 4/2017 | Geiss ............ H04N 5/23212 |
| 2018/0038768 | A1 | 2/2018 | Hofmann et al. |
| 2018/0106700 | A1 | 4/2018 | Limon et al. |
| 2018/0140182 | A1 | 5/2018 | Limon et al. |
| 2019/0072455 | A1 | 3/2019 | Limon et al. |

FOREIGN PATENT DOCUMENTS

| | | |
|---|---|---|
| CN | 101842683 | 9/2010 |
| CN | 103163663 | 6/2013 |
| CN | 103217273 | 7/2013 |
| CN | 203132816 | 8/2013 |
| CN | 103412415 | 11/2013 |
| CN | 105164507 A | 12/2015 |
| DE | 19646360 | 5/1998 |
| DE | 10341161 | 2/2005 |
| DE | 102007057260 | 6/2009 |
| EP | 1679499 | 7/2006 |
| EP | 2608109 | 6/2013 |
| JP | S50-145249 | 11/1975 |
| JP | S58-139044 | 8/1983 |
| JP | S58156828 | 9/1983 |
| JP | S59-67440 | 4/1984 |
| JP | H06258182 A | 9/1994 |
| JP | 09243514 | 9/1997 |
| JP | 2001-21449 | 1/2001 |
| JP | 2006-189386 | 7/2006 |
| JP | 2011-209530 | 10/2011 |
| JP | 2013-127621 | 6/2013 |
| JP | 2015-025859 | 2/2015 |
| KR | 20060093596 | 8/2006 |
| KR | 101528132 | 6/2015 |
| WO | 97/25647 | 7/1997 |
| WO | 2015051573 | 4/2015 |
| WO | 2016141333 | 9/2016 |
| WO | 2016181309 A1 | 11/2016 |
| WO | 2016181310 A1 | 11/2016 |
| WO | 2017125902 A1 | 7/2017 |

OTHER PUBLICATIONS

Notice of Allowance for U.S. Appl. No. 15/572,893, dated Nov. 5, 2019, 12 Pages.
Office Action for Chinese Patent Application No. 201680040458.7, dated Nov. 14, 2019, 35 pages (Including 20 pages of English translation).
Ru Zheng et al., "A device for detecting progressive addition lenses", Optical Technique, vol. 41, Issue 4, chaps.1-3, Jul. 2015, 3 pages.
International Preliminary Report on Patentability for PCT/IB2016/052672, dated Nov. 23, 2017, 6 pages.
International Search Report and Written Opinion for PCT/IB2016/052672, dated Sep. 11, 2016, 8 pages.
International Preliminary Report on Patentability for PCT/IB2016/052673, dated Nov. 23, 2017, 8 pages.
International Search Report and Written Opinion for PCT/IB2016/052673, dated Aug. 29, 2016, 12 pages.
International Search Report and Written Opinion for PCT/IB2017/050338, dated Jun. 14, 2017, 14 pages.
Office Action for U.S. Appl. No. 15/572,893, dated Oct. 22, 2018, 18 pages.
Office Action for Russian Patent Application No. 2017139574, dated Dec. 24, 2018, 15 pages (Including 7 pages of English translation).
European Search Report for European Patent Application No. 16792277.2, dated Jan. 2, 2019, 23 pages.
European Search Report for European Patent Application No. 16792278.0, dated Jan. 7, 2019, 19 pages.
Office Action for U.S. Appl. No. 15/572,893, dated Mar. 18, 2019, 26 pages.
Notice of Allowance for U.S. Appl. No. 15/572,893, dated May 13, 2019, 9 Pages.
Office Action for Russian Patent Application No. 2017139574/28, dated Apr. 25, 2019, 17 pages (Including 8 pages of English translation).
Office Action for Chinese Patent Application No. 201680040458.7, dated Mar. 29, 2019, 12 pages.
European Search Report for European Patent Application No. 16792278.0, dated Apr. 9, 2019, 18 pages.
Office Action for Chinese Patent Application No. 201680040517.0, dated Mar. 29, 2019, 35 pages (Including 20 pages of English translation).
European Search Report for European Patent Application No. 16792277.2, dated Mar. 4, 2019,22 pages.
Office Action for U.S. Appl. No. 15/572,920, dated Jul. 23, 2019, 54 pages.
Notice of Allowance for U.S. Appl. No. 15/767,205, dated Jun. 25, 2019, 36 Pages.
European Search Report for European Patent Application No. 17741169.1, dated Sep. 12, 2019, 8 pages.
Office Action for Russian Patent Application No. 2017139576 dated Sep. 26, 2019, 16 pages (Including 8 pages of English translation).

(56) References Cited

OTHER PUBLICATIONS

Notice of Allowance for U.S. Appl. No. 15/767,205, dated Oct. 23, 2019, 14 Pages.
Office Action for Japanese Patent Application No. 2017-558641, dated Mar. 17, 2020, 11 pages [including 6 pages of English translation].
Office Action for Japanese Patent Application No. 2017-558737, dated Mar. 24, 2020, 10 pages [including 5 pages of English translation].
Office Action for Chinese Patent Application No. 201780018306.1, dated Feb. 3, 2020, 7 pages.

* cited by examiner

– – – – axis of the LUT cylinder

APPARATUS, SYSTEM AND METHOD OF DETERMINING ONE OR MORE OPTICAL PARAMETERS OF A LENS

CROSS REFERENCE

This Application claims the benefit of and priority from U.S. Provisional Patent Application No. 62/159,295 entitled "APPARATUS, SYSTEM AND METHOD OF DETERMINING ONE OR MORE OPTICAL PARAMETERS OF A LENS", filed May 10, 2015, U.S. Provisional Patent Application No. 62/216,757 entitled "APPARATUS, SYSTEM AND METHOD OF DETERMINING ONE OR MORE OPTICAL PARAMETERS OF A LENS", filed Sep. 10, 2015, and U.S. Provisional Patent Application No. 62/286,331 entitled "APPARATUS, SYSTEM AND METHOD OF DETERMINING ONE OR MORE OPTICAL PARAMETERS OF A LENS", filed Jan. 23, 2016, the entire disclosures of all of which are incorporated herein by reference.

TECHNICAL FIELD

Embodiments described herein generally relate to determining one or more optical parameters of a lens.

BACKGROUND

Eyeglasses and/or prescription eyeglasses may include lenses assembled in a frame of the eyeglasses.

The lenses may have one or more optical parameters. The optical parameters of a lens may include, for example, a spherical power, a cylindrical power and/or a cylindrical axis.

Determining the spherical power, the cylindrical power, and/or the cylindrical axis of the lens may be useful, for example, if a user of the eyeglasses wishes to duplicate the eyeglasses and/or to produce spare lenses for the eyeglasses.

BRIEF DESCRIPTION OF THE DRAWINGS

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. The figures are listed below.

DETAILED DESCRIPTION

Figure 1:
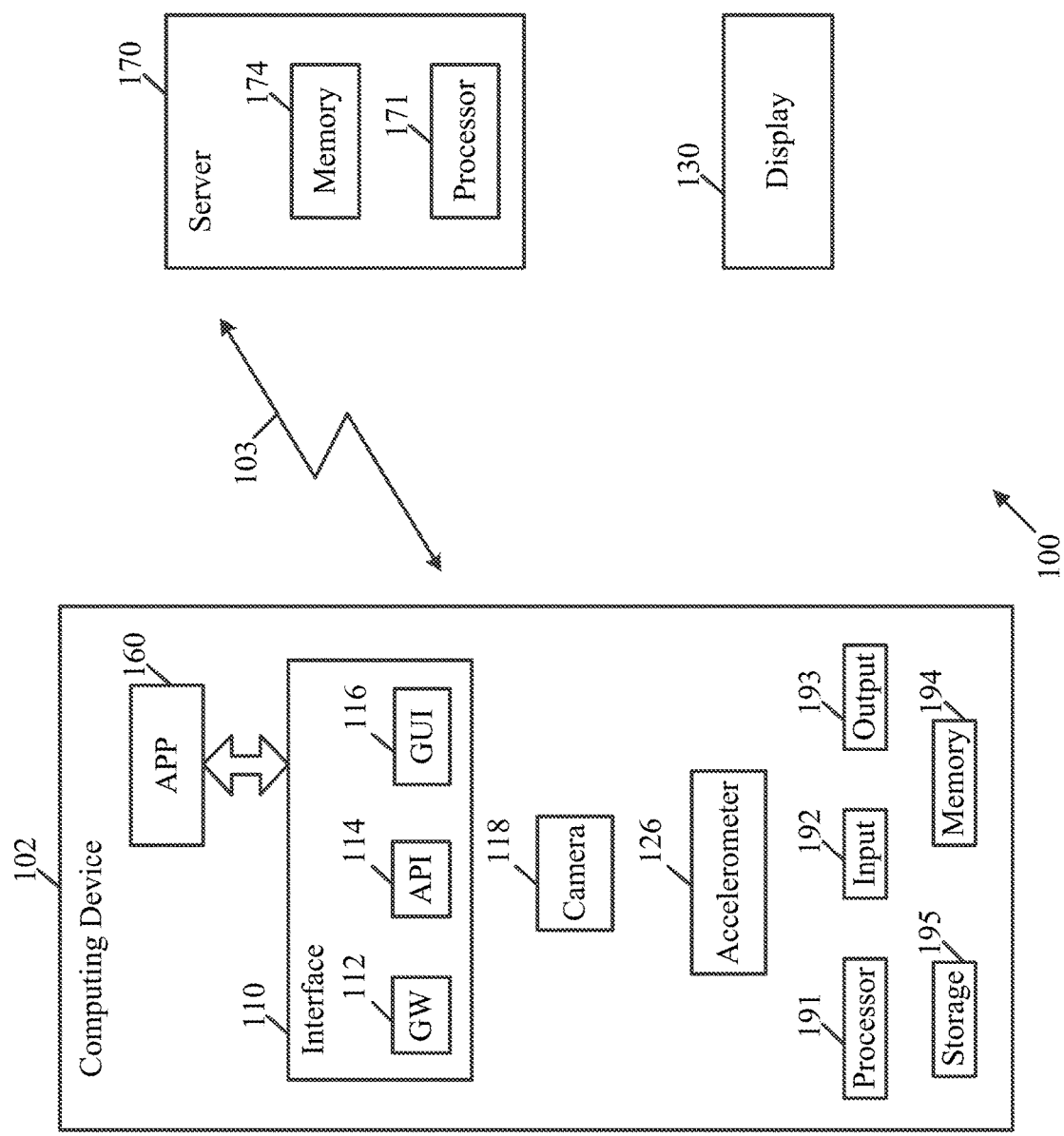
FIG. 1 is a schematic block diagram illustration of a system, in accordance with some demonstrative embodiments.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

Some portions of the following detailed description are presented in terms of algorithms and symbolic representations of operations on data bits or binary digital signals within a computer memory. These algorithmic descriptions and representations may be the techniques used by those skilled in the data processing arts to convey the substance of their work to others skilled in the art.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Discussions herein utilizing terms such as, for example, "processing", "computing", "calculating", "determining", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

The terms "plurality" and "a plurality", as used herein, include, for example, "multiple" or "two or more". For example, "a plurality of items" includes two or more items.

References to "one embodiment", "an embodiment", "demonstrative embodiment", "various embodiments" etc., indicate that the embodiment(s) so described may include a particular feature, structure, or characteristic, but not every embodiment necessarily includes the particular feature, structure, or characteristic. Further, repeated use of the phrase "in one embodiment" does not necessarily refer to the same embodiment, although it may.

As used herein, unless otherwise specified the use of the ordinal adjectives "first", "second", "third" etc., to describe a common object, merely indicate that different instances of like objects are being referred to, and are not intended to imply that the objects so described must be in a given sequence, either temporally, spatially, in ranking, or in any other manner.

Some embodiments, for example, may take the form of an entirely hardware embodiment, an entirely software embodiment, or an embodiment including both hardware and software elements. Some embodiments may be implemented in software, which includes but is not limited to firmware, resident software, microcode, or the like.

Furthermore, some embodiments may take the form of a computer program product accessible from a computer-usable or computer-readable medium providing program code for use by or in connection with a computer or any instruction execution system. For example, a computer-usable or computer-readable medium may be or may include any apparatus that can contain, store, communicate, propagate, or transport the program for use by or in connection with the instruction execution system, apparatus, or device.

In some demonstrative embodiments, the medium may be an electronic, magnetic, optical, electromagnetic, infrared, or semiconductor system (or apparatus or device) or a propagation medium. Some demonstrative examples of a computer-readable medium may include a semiconductor or solid state memory, magnetic tape, a removable computer diskette, a random access memory (RAM), a read-only memory (ROM), a FLASH memory, a rigid magnetic disk, and an optical disk. Some demonstrative examples of optical disks include compact disk—read only memory (CD-ROM), compact disk—read/write (CD-R/W), and DVD.

In some demonstrative embodiments, a data processing system suitable for storing and/or executing program code may include at least one processor coupled directly or indirectly to memory elements, for example, through a system bus. The memory elements may include, for example, local memory employed during actual execution of the program code, bulk storage, and cache memories which may provide temporary storage of at least some program code in order to reduce the number of times code must be retrieved from bulk storage during execution.

In some demonstrative embodiments, input/output or I/O devices (including but not limited to keyboards, displays, pointing devices, etc.) may be coupled to the system either directly or through intervening I/O controllers. In some demonstrative embodiments, network adapters may be coupled to the system to enable the data processing system to become coupled to other data processing systems or remote printers or storage devices, for example, through intervening private or public networks. In some demonstrative embodiments, modems, cable modems and Ethernet cards are demonstrative examples of types of network adapters. Other suitable components may be used.

Some embodiments may include one or more wired or wireless links, may utilize one or more components of wireless communication, may utilize one or more methods or protocols of wireless communication, or the like. Some embodiments may utilize wired communication and/or wireless communication.

Some embodiments may be used in conjunction with various devices and systems, for example, a mobile phone, a Smartphone, a mobile computer, a laptop computer, a notebook computer, a tablet computer, a handheld computer, a handheld device, a Personal Digital Assistant (PDA) device, a handheld PDA device, a mobile or portable device, a non-mobile or non-portable device, a cellular telephone, a wireless telephone, a device having one or more internal antennas and/or external antennas, a wireless handheld device, or the like.

Reference is now made to FIG. 1, which schematically illustrates a block diagram of a system 100, in accordance with some demonstrative embodiments.

As shown in FIG. 1, in some demonstrative embodiments system 100 may include a device 102.

In some demonstrative embodiments, device 102 may be implemented using suitable hardware components and/or software components, for example, processors, controllers, memory units, storage units, input units, output units, communication units, operating systems, applications, or the like.

In some demonstrative embodiments, device 102 may include, for example, a computing device, a mobile phone, a Smartphone, a Cellular phone, a notebook, a mobile computer, a laptop computer, a notebook computer, a tablet computer, a handheld computer, a handheld device, a PDA device, a handheld PDA device, a wireless communication device, a PDA device which incorporates a wireless communication device, or the like.

In some demonstrative embodiments, device 102 may include, for example, one or more of a processor 191, an input unit 192, an output unit 193, a memory unit 194, and/or a storage unit 195. Device 102 may optionally include other suitable hardware components and/or software components. In some demonstrative embodiments, some or all of the components of one or more of device 102 may be enclosed in a common housing or packaging, and may be interconnected or operably associated using one or more wired or wireless links In other embodiments, components of one or more of device 102 may be distributed among multiple or separate devices.

In some demonstrative embodiments, processor 191 may include, for example, a Central Processing Unit (CPU), a Digital Signal Processor (DSP), one or more processor cores, a single-core processor, a dual-core processor, a multiple-core processor, a microprocessor, a host processor, a controller, a plurality of processors or controllers, a chip, a microchip, one or more circuits, circuitry, a logic unit, an Integrated Circuit (IC), an Application-Specific IC (ASIC), or any other suitable multi-purpose or specific processor or controller. Processor 191 may execute instructions, for example, of an Operating System (OS) of device 102 and/or of one or more suitable applications.

In some demonstrative embodiments, input unit 192 may include, for example, a keyboard, a keypad, a mouse, a touch-screen, a touch-pad, a track-ball, a stylus, a microphone, or other suitable pointing device or input device. Output unit 193 may include, for example, a monitor, a screen, a touch-screen, a flat panel display, a Light Emitting Diode (LED) display unit, a Liquid Crystal Display (LCD) display unit, a plasma display unit, one or more audio speakers or earphones, or other suitable output devices.

In some demonstrative embodiments, memory unit 194 includes, for example, a Random Access Memory (RAM), a Read Only Memory (ROM), a Dynamic RAM (DRAM), a Synchronous DRAM (SD-RAM), a flash memory, a volatile memory, a non-volatile memory, a cache memory, a buffer, a short term memory unit, a long term memory unit, or other suitable memory units. Storage unit 195 may include, for example, a hard disk drive, a floppy disk drive, a Compact Disk (CD) drive, a CD-ROM drive, a DVD drive, or other suitable removable or non-removable storage units. Memory unit 194 and/or storage unit 195, for example, may store data processed by device 102.

In some demonstrative embodiments, device 102 may be configured to communicate with one or more other devices via a wireless and/or wired network 103.

In some demonstrative embodiments, network 103 may include a wired network, a local area network (LAN), a wireless LAN (WLAN) network, a radio network, a cellular network, a Wireless Fidelity (WiFi) network, an IR network, a Bluetooth (BT) network, and the like.

In some demonstrative embodiments, device 102 may allow one or more users to interact with one or more processes, applications and/or modules of device 102, e.g., as described herein.

In some demonstrative embodiments, device 102 may be configured to perform and/or to execute one or more operations, modules, processes, procedures and/or the like.

In some demonstrative embodiments, device 102 may be configured to determine a one or more optical parameters of a lens of eyeglasses, e.g., provided by a user of device 102, e.g., as described below.

In some demonstrative embodiments, system 100 may be configured to perform lensmeter or lensometer analysis of the lens of the eyeglasses, for example, even without using any auxiliary optical means, e.g., as described below.

In some demonstrative embodiments, the one or more optical parameters of the lens may include a spherical power, a cylindrical power and/or a cylindrical axis of the lens.

In some demonstrative embodiments, the one or more optical parameters of the lens may include a pupillary distance between a pair of lenses assembled in a frame of the eyeglasses.

In some demonstrative embodiments, system 100 may be configured to analyze a focal power of a spherical lens, a focal power and an axis of a cylindrical lens, and/or a distance between the centers of two lenses assembled in a frame of the eyeglasses, e.g., as described below.

In some demonstrative embodiments, system 100 may include at least one service, module, controller, and/or application 160 configured to determine the one or more optical parameters of the lens of the user of device 102, e.g., as described below.

In some demonstrative embodiments, application 160 may include, or may be implemented as, software, a software module, an application, a program, a subroutine, instructions, an instruction set, computing code, words, values, symbols, and the like.

In some demonstrative embodiments, application 160 may include a local application to be executed by device 102. For example, memory unit 194 and/or storage unit 195 may store instructions resulting in application 160, and/or processor 191 may be configured to execute the instructions resulting in application 160, e.g., as described below.

In other embodiments, application 160 may include a remote application to be executed by any suitable computing system, e.g., a server 170.

In some demonstrative embodiments, server 170 may include at least a remote server, a web-based server, a cloud server, and/or any other server.

In some demonstrative embodiments, the server 170 may include a suitable memory and/or storage unit 174 having stored thereon instructions resulting in application 160, and a suitable processor 171 to execute the instructions, e.g., as descried below.

In some demonstrative embodiments, application 160 may include a combination of a remote application and a local application.

In one example, application 160 may be downloaded and/or received by the user of device 102 from another computing system, e.g., server 170, such that application 160 may be executed locally by users of device 102. For example, the instructions may be received and stored, e.g., temporarily, in a memory or any suitable short-term memory or buffer of device 102, e.g., prior to being executed by processor 191 of device 102.

In another example, application 160 may include a frontend to be executed locally by device 102, and a backend to be executed by server 170. For example, one or more first operations of determining the one or more optical parameters of the lens of the user may be performed locally, for example, by device 102, and/or one or more second operations of determining the one or more optical parameters may be performed remotely, for example, by server 170, e.g., as described below.

In other embodiments, application 160 may include any other suitable computing arrangement and/or scheme.

In some demonstrative embodiments, system 100 may include an interface 110 to interface between a user of device 102 and one or more elements of system 100, e.g., application 160.

In some demonstrative embodiments, interface 110 may be implemented using any suitable hardware components and/or software components, for example, processors, controllers, memory units, storage units, input units, output units, communication units, operating systems, and/or applications.

In some embodiments, interface 110 may be implemented as part of any suitable module, system, device, or component of system 100.

In other embodiments, interface 110 may be implemented as a separate element of system 100.

In some demonstrative embodiments, interface 110 may be implemented as part of device 102. For example, interface 110 may be associated with and/or included as part of device 102.

In one example, interface 110 may be implemented, for example, as middleware, and/or as part of any suitable application of device 102. For example, interface 110 may be implemented as part of application 160 and/or as part of an OS of device 102.

In some demonstrative embodiments, interface 160 may be implemented as part of server 170. For example, interface 110 may be associated with and/or included as part of server 170.

In one example, interface 110 may include, or may be part of a Web-based application, a web-site, a web-page, a plug-in, an ActiveX control, a rich content component (e.g., a Flash or Shockwave component), or the like.

In some demonstrative embodiments, interface 110 may be associated with and/or may include, for example, a gateway (GW) 112 and/or an application programming interface (API) 114, for example, to communicate information and/or communications between elements of system 100 and/or to one or more other, e.g., internal or external, parties, users, applications and/or systems.

In some embodiments, interface 110 may include any suitable Graphic-User-Interface (GUI) 116 and/or any other suitable interface.

In some demonstrative embodiments, system 100 may include a display 130 configured to display one or more objects to be captured by an image capturing device, and/or to display information, objects, instructions and/or any other content, for example, to a user, e.g., as described below.

In some demonstrative embodiments, display 130 may include a separate display, a stand-alone display and/or a display device, e.g., separate from other elements of system 100.

In some demonstrative embodiments, display 130 may be part of device 102 or part of server 170.

In some demonstrative embodiments, display 130 may be part of any other computing system, e.g., a laptop, a desktop, and/or the like.

In some demonstrative embodiments, display 130 may include, for example, a monitor, a screen, a touch-screen, a flat panel display, a LED display unit, an LCD display unit, a plasma display unit, one or more audio speakers or earphones, and/or any other suitable components.

In some demonstrative embodiments, the GUI 116 of interface 110 may be displayed on display 130.

In some demonstrative embodiments, application 160 may be configured to determine the one or more optical parameters of the lens, for example, based on at least one captured image of an object, e.g., as described below.

In some demonstrative embodiments, the object may include an object having one or more known dimensions, e.g., as described below.

In some demonstrative embodiments, application 160 may be configured to determine the one or more optical parameters of the lens, for example, based on the dimensions of the object, e.g., as described below.

In some demonstrative embodiments, the object may include a circularly symmetric or rotationally symmetric object, e.g., as described below.

In some demonstrative embodiments, the object may be displayed on display 130.

In other embodiments, the object may include an object which is not displayed on display 130, e.g., the object may include a physical object, which may be placed, presented, and/or positioned, for example, to enable device 102 to capture the image of the object, e.g., as described below.

In some demonstrative embodiments, application 160 may be configured to control, cause, trigger, and/or instruct display 130 to display the object.

In some demonstrative embodiments, application 160 may be configured to calibrate a display size of the object on display 130, e.g., as described below.

In some demonstrative embodiments, the captured image may be captured by the user, and may include the object, e.g., as described below.

In some demonstrative embodiments, the captured image of the object may be captured via the lens of the eyeglasses.

In some demonstrative embodiments, device 102 may include an image capturing device, e.g., a camera 118 or any other device, configured to capture the at least one image.

In some demonstrative embodiments, application 160 may be configured to control, cause, trigger, and/or instruct camera 118 to capture the at least one image including the object.

In some demonstrative embodiments, application 160 may be configured to instruct the user to capture at least one image of the object via the lens of the eyeglasses.

In some demonstrative embodiments, application 160 may be configured to control, cause, trigger, and/or instruct camera 118 to capture the at least one image via the center of the lens, or via any other part of the lens.

In some demonstrative embodiments, an image of the object, as may be seen by the camera 118, e.g., through the lens, may be displaced laterally, for example, if the image is not viewed via the center of the lens.

In some demonstrative embodiments, a displacement of the image may vary, for example, according to the distance from the center of the lens, and/or the spherical power of the lens.

In some demonstrative embodiments, a center of an object displayed on display 130 may be imaged without displacement, e.g., with or without the lens, for example, if an optical axis connecting between the lens of camera 118 and the center of the object displayed on display 130 coincides with the center of the lens.

In some demonstrative embodiments, the center of the lens may be identified, for example, by moving the lens to a distance, at which the center of the object displayed on display 130 overlaps with the center of the object, e.g., when imaged through the lens.

In some demonstrative embodiments, the spherical power of the lens, and/or a sign of the lens, e.g., a plus (converging) lens or a minus (diverging) lens, may be estimated, for example, based on an amount of displacement of the image, for example, when keeping the lens at a fixed location.

In some demonstrative embodiments, two centers of the object, e.g., a first center when using the lens and a second center when not using the lens, may be displayed on the screen without displacement, for example, if an image is captured through the center of the lens. However, sizes and distortions in one or more features of the images may result in other images, e.g., which are not captured through the center of the lens.

In some demonstrative embodiments, application 160 may be configured to determine the one or more optical parameters of the lens based on the at least one captured image, e.g., as described below.

In some demonstrative embodiments, application 160 may be configured to receive the at least one image of the object captured via the lens of the eyeglasses, e.g., from the camera 118.

In one example, application 160 may be configured to determine the one or more optical parameters of the lens locally, for example, if application 160 is locally implemented by device 102. According to this example, camera 118 may be configured to capture the image, and application 160 may be configured to receive the captured image, e.g., from camera 118, and to determine the one or more optical parameters of the lens, e.g., as described below.

In another example, application 160 may be configured to determine the one or more optical parameters of the lens remotely, for example, if application 160 is implemented by server 170, or if the back-end of application 160 is implemented by server 170, e.g., while the front-end of application 160 is implemented by device 102. According to this example, camera 118 may be configured to capture the image; the front-end of application 160 may be configured to receive the captured image; and server 170 and/or the back-end of application 160 may be configured to determine the one or more optical parameters of the lens, e.g., based on information received from the front-end of application 160.

In one example, device 102 and/or the front-end of application 160 may be configured to send the captured image and, optionally, additional information, e.g., as described below, to server 170, e.g., via network 103; and/or server 170 and/or the back-end of application 160 may be configured to receive the captured image, and to determine the one or more optical parameters of the lens, for example, based on the captured image from device 102.

In some demonstrative embodiments, application 160 may be configured to determine the one or more optical parameters of the lens, for example, based on autofocus information of camera 118, when the image is captured.

In some demonstrative embodiments, application 160 may be configured to determine the spherical power of the lens, for example, based on the autofocus information of camera 118, when the image is captured.

In some demonstrative embodiments, the spherical power of the lens may be determined, for example, based on a displacement of camera 118 and a captured image via the center of the lens, e.g., as described below.

In some demonstrative embodiments, application 160 may be configured to receive a captured image of an object, e.g., displayed on display 130, when captured, for example, through the lens, e.g., through the center of the lens.

In some demonstrative embodiments, application 160 may be configured to analyze, for example, an amount of a dioptric change, e.g., from a movement of the auto focus (AF) lens of camera 118.

In some demonstrative embodiments, the dioptric change may enable camera 118, for example, to capture a sharp image of the object at the distance at which the sharp image is captured.

In some demonstrative embodiments, the spherical power of the lens may be based on the AF setting, e.g., the AF movement, of camera 118, when capturing the image of the object.

In some demonstrative embodiments, application 160 may be configured to determine, for example, if an addition of the spherical power of the lens of the eyeglasses to the power of the camera lens of camera 118 is compensated by the AF of camera 118, e.g., at the same amount.

In some demonstrative embodiments, a total power, denoted $\varnothing_{total}$, of two lenses, denoted $\varnothing_1$, $\varnothing_2$, separated by a distance, denoted t, with an index of refraction, denoted n, may be determined, e.g., as follows:

$$\phi_{total} = \phi_1 + \phi_2 - \phi_1 * \phi_2 * \frac{t}{n} \quad (1)$$

In one example, if a lens of camera 118 ("the camera lens") is focused at 50 centimeters (cm) to the object, the AF may move the camera lens, for example, to accommodate a change of +2.00 Diopter (D).

According to this example, if a lens of eyeglasses ("the eyeglasses lens") having a focal length of 100 mm (−10 D) may be in contact with the camera lens at a distance t=0, the AF may accommodate a change of 12.00 D.

In some demonstrative embodiments, if the eyeglasses lens is removed, and the focus of the camera remains at 12 D, a sharpest distance from the object, e.g., a distance which enables to view the object most sharply compared to other distances, may be at 83.33 millimeter (mm), e.g., $$\frac{1000}{12.00D} = 83.33 \text{ (mm)}.$$

In some demonstrative embodiments, the sharpest distance, which enables to view the object most sharply, e.g., 83.33 mm, may be read from camera 118, e.g., the AF information of camera 118.

In some demonstrative embodiments, application 160 may be configured to perform one or more operations to determine the spherical power of the lens, for example, based on the autofocus information of camera 118, e.g., as described below.

Figure 2:
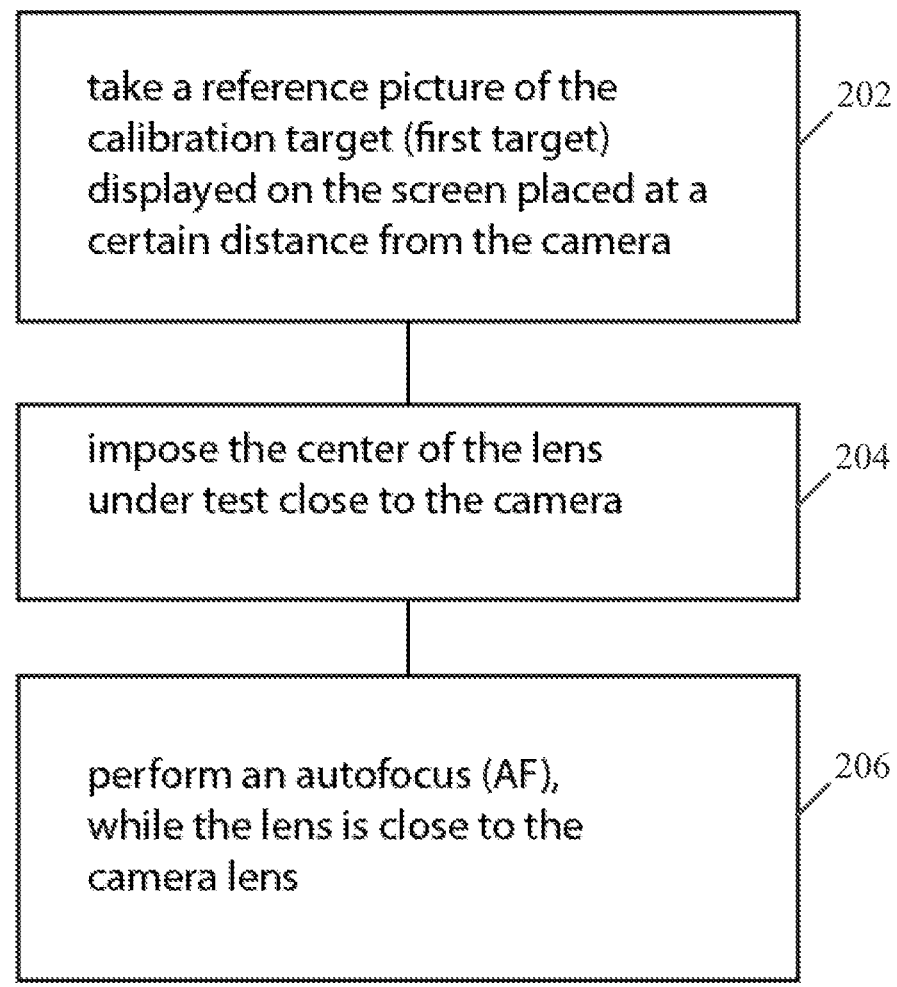
FIG. 2 is a schematic flow-chart illustration of a method of capturing an image via a lens using an autofocus (AF), in accordance with some demonstrative embodiments.

Reference is made to FIG. 2, which schematically illustrates a method of capturing an image via a lens using an AF, in accordance with some demonstrative embodiments. For example, one or operations of the method of FIG. 2 may be performed by a system, e.g., system 100 (FIG. 1), a mobile device, device 102 (FIG. 1), a server, e.g., server 170 (FIG. 1), a display (FIG. 1), and/or an application, e.g., application 160 (FIG. 1).

As indicated at block 202, the method may include taking a reference picture of an object displayed on a display, which is placed at a distance from the camera. For example, application 160 (FIG. 1) may cause camera 118 (FIG. 1) to capture the image of the object displayed on display 130 (FIG. 1), e.g., as described above.

As indicated at block 204, the method may include imposing the center of the eyeglasses lens close to the camera lens. For example, application 160 (FIG. 1) may instruct the user to impose the center of the eyeglasses lens close to the camera lens of camera 118 (FIG. 1).

As indicated at block 206, the method may include performing an autofocus (AF) procedure of the camera, for example, while the eyeglasses lens is close to the camera lens. For example, application 160 (FIG. 1) may instruct camera 118 (FIG. 1) to capture an image, e.g., while performing autofocus, for example, when the eyeglasses lens is close to the camera lens.

Refereeing back to FIG. 1, in some demonstrative embodiments application 160 may be configured to determine the spherical power of the lens, for example, based on the autofocus information of camera 118, e.g., as described below.

In some demonstrative embodiments, application 160 may be configured to determine the spherical power of the lens based on a direct distance AF ("direct AF") method and/or an indirect distance AF ("indirect AF") method, e.g., as described below.

In some demonstrative embodiments, according to the direct distance AF method the lens power may be determined based on the AF change of the camera 118, e.g., as described below.

In some demonstrative embodiments, an image of the object may be captured without the lens and may be set as the reference image.

In some demonstrative embodiments, another image of the object may be captured with the lens.

In some demonstrative embodiments, application 160 may be configured to perform one or more operations according to the direct AF method.

In some demonstrative embodiments, application 160 may be configured to determine a power of the lens based on the AF information of camera 118, e.g., when at least one image of the object is captured by camera 118, e.g., as described below.

In some demonstrative embodiments, application 160 may be configured to process a first image of the object captured via the lens at a first distance between the object and camera 118.

In some demonstrative embodiments, application 160 may be configured to process a second image of the object captured without the lens at a second distance between the object and camera 118.

In some demonstrative embodiments, application 160 may be configured to determine a power of the lens based on the first and second distances, first autofocus information of camera 118 when the first image is captured, and second autofocus information of camera 118 when the second image is captured, e.g., as described below.

Figure 3:
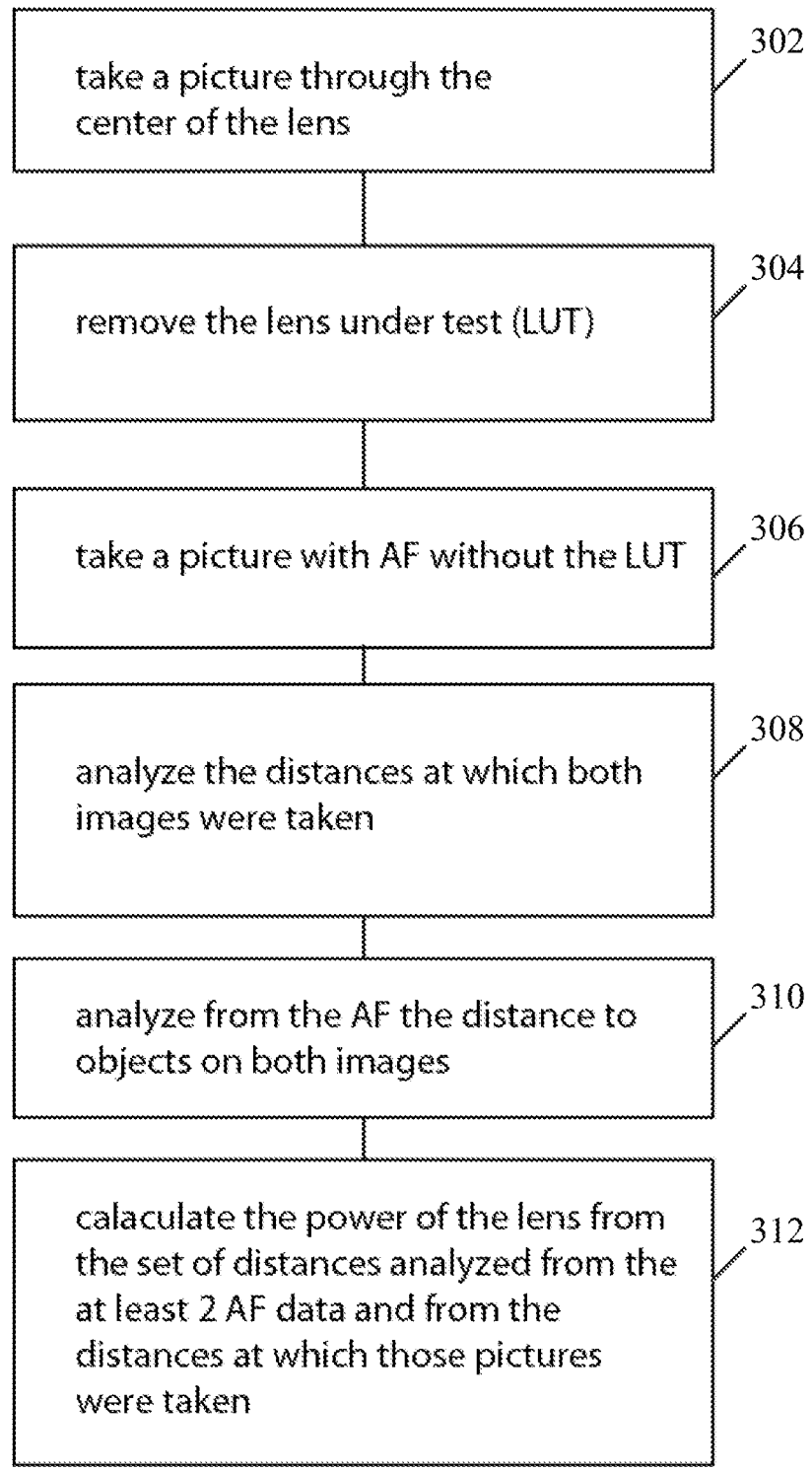
FIG. 3 is a schematic flow-chart illustration of a method of determining a power of a lens based on autofocus information, in accordance with some demonstrative embodiments.

Reference is made to FIG. 3, which schematically illustrates a method of determining a power of a lens based on autofocus information, in accordance with some demonstrative embodiments. For example, one or operations of the method of FIG. 3 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, application 160 (FIG. 1) may perform one or more, e.g., all, of the operations of FIG. 3, for example, to determine a power of the lens based on the autofocus information, e.g., according to the direct AF method.

As indicated at block 302, the method may include capturing a first image of an object through the center of the lens. For example, application 160 (FIG. 1) may cause camera 118 (FIG. 1) to capture the first image of an object, e.g., the object displayed on display 130 (FIG. 1) and/or another object, e.g., a physical object, via the center of the lens, e.g., as described above.

As indicated at block 304, the method may include removing the lens. For example, application 160 (FIG. 1) may instruct the user to remove the lens.

As indicated at block 306, the method may include capturing a second image of the object, e.g., the object displayed on display 130 (FIG. 1) and/or another object, e.g., a physical object, without the lens. For example, application 160 (FIG. 1) may cause camera 118 (FIG. 1) to capture the second image of the object displayed on display 130 (FIG. 1) without the lens, e.g., as described above.

As indicated at block 308, the method may include determining a first distance between the camera and the display when the first image was captured, and a second distance between the camera and the display when the second image was captured. For example, application 160 (FIG. 1) may determine the first and second distances.

As indicated at block 310, the method may include processing first autofocus information when capturing the first image and second autofocus information when capturing the second image. For example, application 160 (FIG. 1) may process the first and second autofocus information, e.g., from camera 118.

As indicated at block 312, the method may include calculating the power of the lens, for example, based on the first and second distances, and the first and second autofocus information. For example, application 160 (FIG. 1) may determine the spherical power of the lens, for example, based on the first and second distances, and the first and second autofocus information, e.g., as described above.

Referring back to FIG. 1, in some demonstrative embodiments, application 160 may be configured to determine the spherical power of the lens based on the indirect AF method.

In some demonstrative embodiments, according to the indirect AF method the lens power may be determined based on a sharpness analysis or a blur analysis, for example, while keeping the autofocus off, or in a manual mode, e.g., as described below.

In some demonstrative embodiments, an image of the object may be captured without the lens and may be set as the reference image.

In some demonstrative embodiments, a set of images may be captured through the lens at different lateral displacements, e.g., displacements of the camera and/or the lens, may be captured, for example, after placing the lens in the line between the lens and the center of the object displayed on the display 130, e.g., while autofocus is off.

In some demonstrative embodiments, the set of images may be used to locate a sharpest image, or a least-blurred image, of the set of images.

In some demonstrative embodiments, the sharpest image may be used to determine the power of the lens.

In some demonstrative embodiments, application 160 may be configured to perform one or more operations to determine the spherical power of the lens based on the indirect AF method, e.g., as described below.

In some demonstrative embodiments, application 160 may be configured to determine the power of the lens based on a sharpness parameter and/or a blur parameter of one or more spatial frequencies in the image of the object, e.g., as described below.

In some demonstrative embodiments, application 160 may be configured to process a plurality of images of the object captured not via the lens at a respective plurality of distances between the object and camera 118.

In some demonstrative embodiments, application 160 may be configured to determine a sharpest image, or a least-blurred image, of the plurality of images including the one or more spatial frequencies.

In some demonstrative embodiments, application 160 may be configured to determine the power of the lens, for example, based at least on a first distance between the object and camera 118, when the sharpest image is captured and a second distance between the object and camera 118, when the image of the object is captured via the lens.

Figure 4:
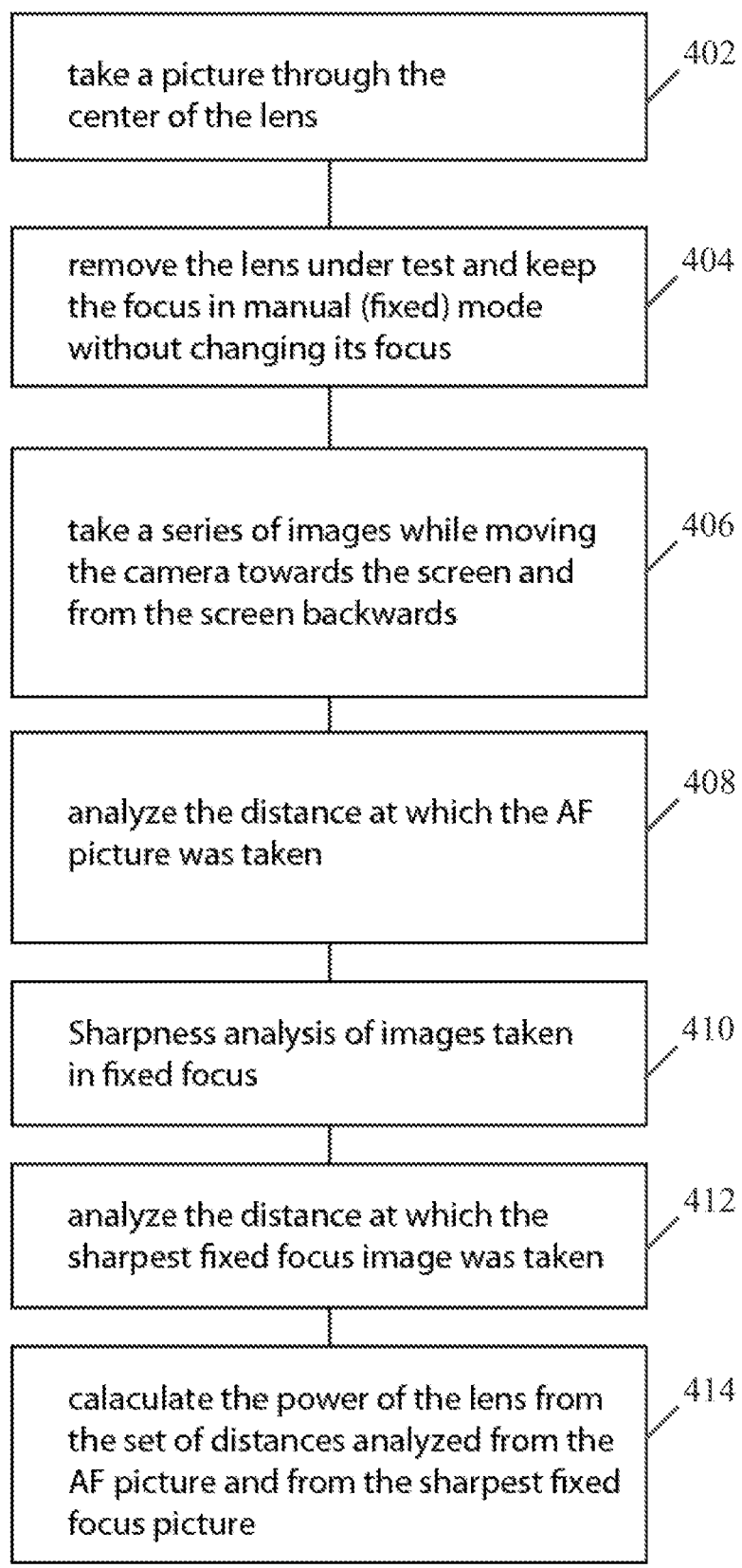
FIG. 4 is a schematic flow-chart illustration of a method of determining a power of a lens, in accordance with some demonstrative embodiments.

Reference is made to FIG. 4, which schematically illustrates a method of determining a power of a lens, in accordance with some demonstrative embodiments. For example, one or operations of the method of FIG. 4 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

In some demonstrative embodiments, application 160 (FIG. 1) may perform one or more, e.g., all, of the operations of FIG. 4, for example, to determine the spherical power of the lens based on the sharpness parameter, e.g., according to the indirect AF method.

As indicated at block 402, the method may include capturing a first image via the lens of an object displayed on the display, e.g., via the center of the lens. For example, application 160 (FIG. 1) may cause camera 118 (FIG. 1) to capture the first image of an object, e.g., the object displayed on display 130 (FIG. 1), and/or another abject, e.g., a physical object, via the center of the lens, e.g., as described above.

As indicated at block 404, the method may include removing the lens and keeping the AF off or in manual mode. For example, application 160 (FIG. 1) may instruct the user to remove the lens and to keep the AF of camera 118 (FIG. 1) off or in manual mode.

As indicated at block 406, the method may include capturing a series of images of the object without the lens, while moving the camera towards the display and/or from the display backwards, e.g., when the object is displayed on the display, or while moving the camera towards the object and/or from the object backwards, e.g., when the object is a physical object. For example, application 160 (FIG. 1) may cause camera 118 (FIG. 1) to capture the plurality of images of the object displayed on display 130 (FIG. 1), e.g., while instructing the user to move camera 118 (FIG. 1), e.g., as described above.

As indicated at block 408, the method may include determining a first distance between the camera and the display when the first image was captured via the lens. For example, application 160 (FIG. 1) may determine the first distance.

As indicated at block 410, the method may include analyzing the series of the images, which were not captured via the lens, for example, to determine a sharpest image, or a least-blurred image, of the series of captured images, e.g., compared to other images of the series. For example, application 160 (FIG. 1) may determine the sharpest image, e.g., as described above.

As indicated at block 412, the method may include determining a second distance, from which the sharpest image was captured. For example, application 160 (FIG. 1) may determine the second distance when the sharpest image is captured, e.g., as described above.

As indicated at block 414, the method may include calculating the power of the lens, for example, based on the first and second distances. For example, application 160 (FIG. 1) may determine the spherical power of the lens, for example, based on the first and second distances, e.g., as described above.

Referring back to FIG. 1, one or more additional or alternative methods may be implemented to analyze the spherical power of a lens, for example, using a relative magnification analysis, e.g., as described below.

In some demonstrative embodiments, application 160 may be configured to determine the power of the lens, for example, based on the one or more dimensions of the object, e.g., as described below.

In some demonstrative embodiments, application 160 may be configured to determine one more imaged dimensions of the object in the image.

In some demonstrative embodiments, application 160 may be configured to determine the spherical power of the lens, for example, based on a magnification between the one or more dimensions of the object and the imaged dimensions of the object in the image, e.g., as described below.

In some demonstrative embodiments, a magnification, denoted M, of a lens may change, for example, according to a power of the lens, denoted $P_{LUT}$, and a distance between the eyeglasses lens and the camera, denoted t, e.g., as follows:

$$P = P_{LUT} + P_{camera} - t * P_{LUT} * P_{camera} \quad (2)$$

$$\phi_1 + P = \phi_2$$

$$M = \frac{\phi_1}{\phi_2}$$

wherein $\emptyset_1$ denotes the vergence, e.g., 1 over the distance, just before the lens; $\emptyset_2$ denotes the vergence just after the camera lens, and n denotes an index of refraction of the medium between the eyeglasses lens and the camera lens, e.g., n may be taken as 1 for air.

In some demonstrative embodiments, the power $P_{LUT}$ of the lens may be determined based on the camera magnification M, e.g., of the target object displayed on the display or the physical object, the mergence before the lens, e.g., given from a measured distance, and an optical power of the lens, denoted $P_C$, which may be given or previously calibrated, and the distance t from the camera 118, as follows:

$$P_{LUT} = \frac{\left(\phi_1 * \left(\frac{1}{M} - 1\right) - P_{camera}\right)}{(1 - t * P_{camera})} \quad (3)$$

In some demonstrative embodiments, the distance t of the lens from the camera may be calculated from the captured image, for example, if a calibration procedure is performed to set a size parameter of the frame, for example, the frame may be placed on the display plane and an object with known dimensions may be displayed over the display 130, e.g., as described below.

In some demonstrative embodiments, application 160 may be configured to determine a distance between the object and the camera 118, for example, when the image is captured via the lens, e.g., via center of the lens.

In some demonstrative embodiments, application 160 may be configured to determine the distance, for example, to be used in determining the one or more optical parameters of the lens, for example, based on the direct autofocus method, the indirect autofocus method, and/or the one or more dimensions of the object.

In some demonstrative embodiments, application 160 may be configured to determine the distance between camera 118 and the object, for example, based on acceleration information indicating an acceleration of camera 118 and/or device 102, e.g., as described below.

In some demonstrative embodiments, device 102 may include an accelerometer 126 configured to provide to application 160 the acceleration information of camera 118 and/or device 102.

In some demonstrative embodiments, application 160 may be configured to determine the distance between camera 118 and the object, for example, based on the one or more dimensions of the object, e.g., which may include known dimensions.

In some demonstrative embodiments, a distance between camera 118 to the object, denoted camera_object_distance, may be determined, for example, based on a focal length, denoted efl, of camera 118, which may be given or calibrated, and a distance, denoted pitch between two adjacent pixels of a camera sensor of camera 118, e.g., as follows:

$$\text{camera\_object\_distance} \cong \frac{efl * h}{h'} = \frac{efl}{\text{pitch}} * \frac{h}{h'\_\text{pixel\_estimated}} \quad (4)$$

wherein h denotes a known dimension of the object, and h'_pixels_estimated denotes the amount of pixels including the dimension in the image, and while using an approximation of:

$$\text{camera\_object\_distance} \gg \textit{efl} \overset{\square}{\Longrightarrow} v \cong \textit{efl}. \quad (5)$$

In some demonstrative embodiments, application 160 may be configured to determine the distance between camera 118 and the object, for example, based on at least two images captured at two or more locations, which differ from one another by a known or measured distance. In one example, a dual camera may be used to capture two images spaced by a predefined distance. In another example, a camera, e.g., camera 118, may be used to take two snapshots, which may be displaced by a certain distance one from another. The distance may be measured, for example, based on accelerometer data from accelerometer 126 and/or using a triangulation method. In other embodiments, application 160 may be configured to determine the distance between camera 118 and the object, for example, according to any other additional or alternative distance estimation method.

In some demonstrative embodiments, application 160 may be configured to determine the cylindrical axis of the lens, e.g., as described below.

In some demonstrative embodiments, application 160 may be configured to determine whether or not the lens includes a cylindrical lens, and to determine the axis of the lens, for example, if the lens includes the cylindrical lens, e.g., as described below.

In some demonstrative embodiments, application 160 may be configured to identify an existence of a cylindrical axis of the lens, for example, based on one or more visual affects of one or more spatial frequencies in the image, e.g., as descried below.

In some demonstrative embodiments, application 160 may be configured to identify an angle of a non-symmetrical blur of the one or more spatial frequencies in the image.

In some demonstrative embodiments, application 160 may be configured to determine the existence of the cylindrical axis, for example, based on the angle of the non-symmetrical blur.

In some demonstrative embodiments, application 160 may be configured to identify an angle of a sharpest portion of the spatial frequencies in the image.

In some demonstrative embodiments, application 160 may be configured to determine the existence of the cylindrical axis, for example, based on the angle of the sharpest portion.

Figure 5:
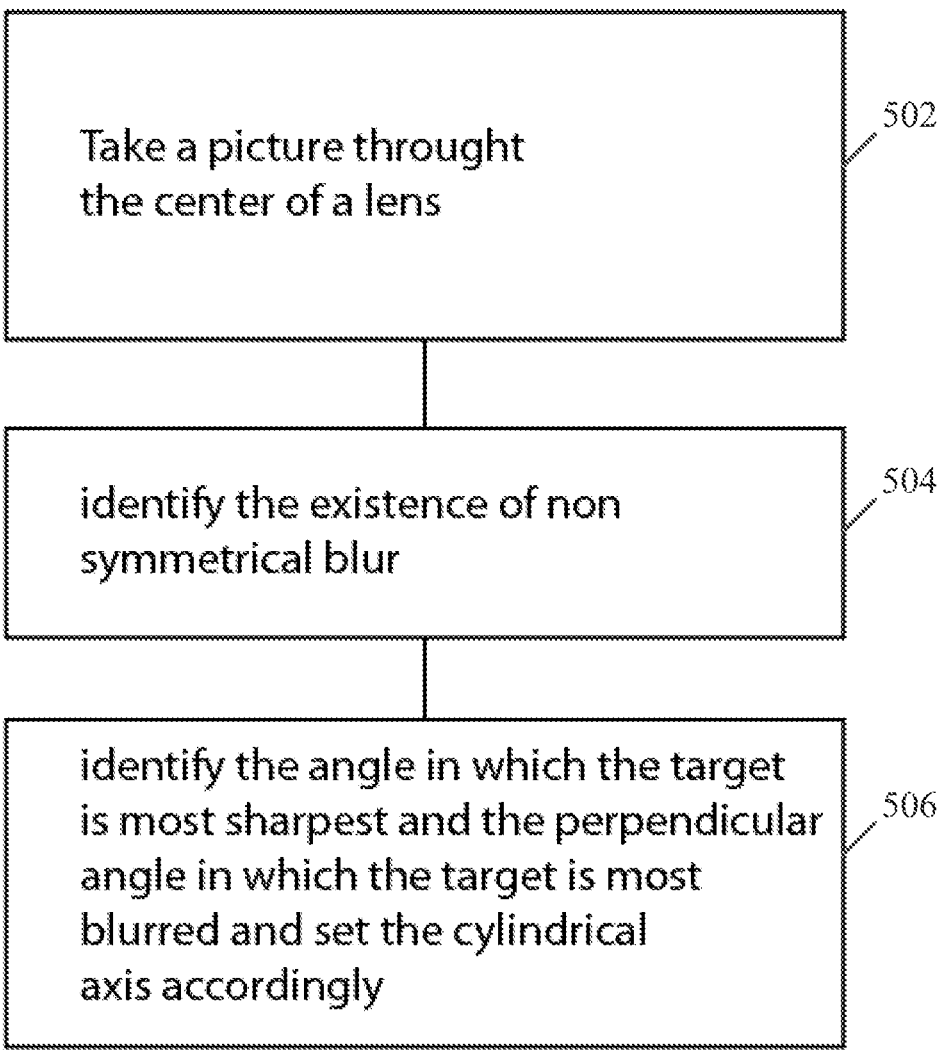
FIG. 5 is a schematic flow-chart illustration of a method of detecting a cylindrical lens and determining the axis of the cylindrical lens, in accordance with some demonstrative embodiments.

Reference is made to FIG. 5, which schematically illustrates a method of detecting a cylindrical lens and determining the axis of the cylindrical lens, in accordance with some demonstrative embodiments. For example, one or operations of the method of FIG. 5 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

As indicated at block 502, the method may include capturing at least one image of an object, e.g., an object displayed on a display and/or another object, e.g., a physical object, via the lens, e.g., through the center of the lens. For example, application 160 (FIG. 1) may cause camera 118 (FIG. 1) to capture the image of the object displayed on display 130 (FIG. 1), for example, via the center of the lens, e.g., as described above.

As indicated at block 504, the method may include identifying a visual effect in the captured image, e.g., an existence of a non-symmetrical blur in the image. For example, application 160 (FIG. 1) may identify the non-symmetrical blur in the image, e.g., as described below.

As indicated at block 506, the method may include identifying an angle at which the imaged object is sharpest, e.g., compared to other angles, and a perpendicular angle, at which the imaged object is most blurred, e.g., compared to other angles. For example, application 160 (FIG. 1) may identify the sharpest angle, and/or the non-symmetrical blur angle, e.g., as described below.

As also indicated at block 506, the method may include setting the cylindrical axis based on the identified angle and/or the identified perpendicular angle. For example, application 160 (FIG. 1) may identify the cylindrical axis based on the sharpest angle and/or the angle of the non-symmetrical blur, e.g., as described below.

Figure 6:
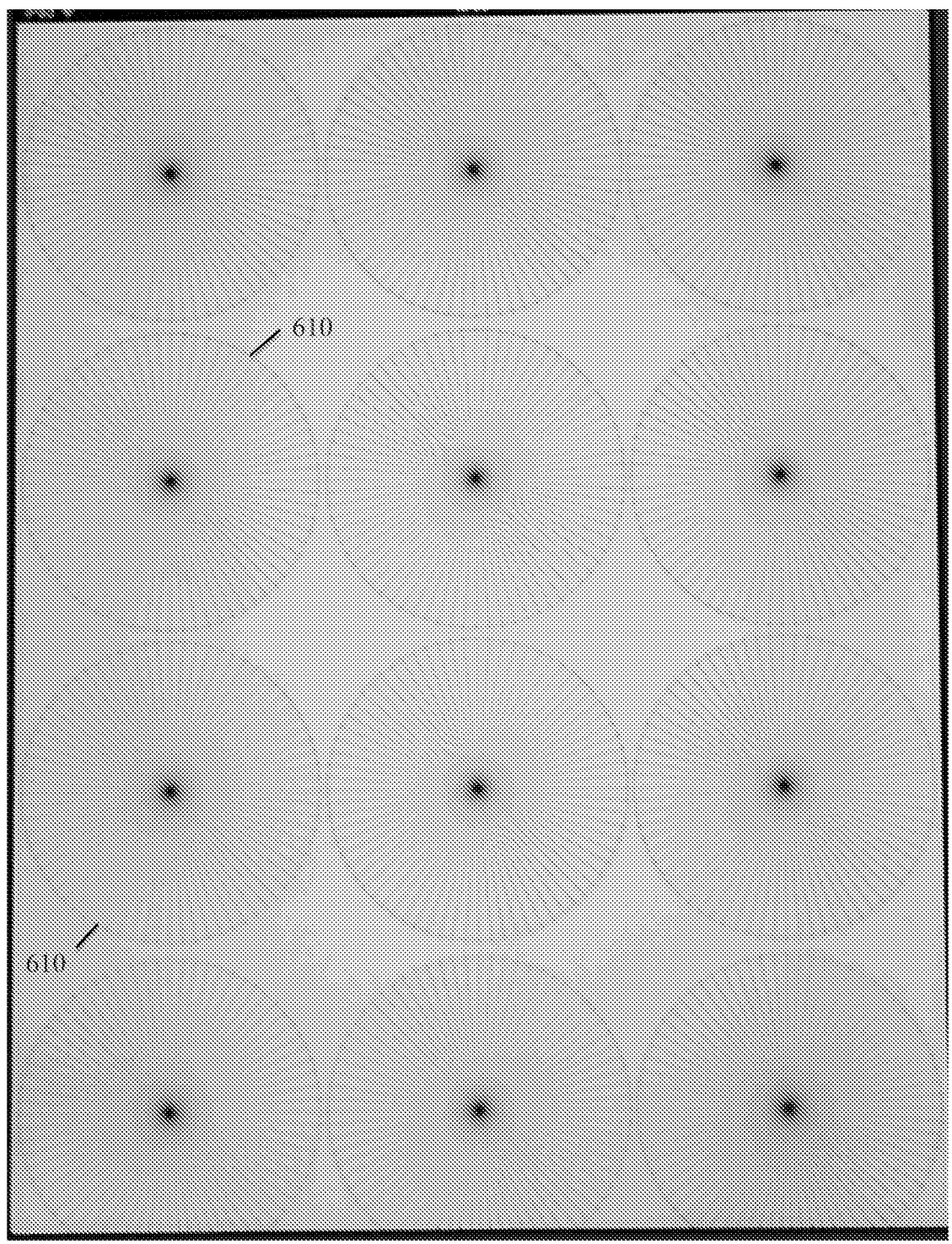
FIG. 6 is a schematic illustration of a plurality of captured images of an object, in accordance with some demonstrative embodiments.

Reference is made to FIG. 6, which schematically illustrates a plurality of captured images 600 of an object 610, in accordance with some demonstrative embodiments.

In some demonstrative embodiments, as shown in FIG. 6, the object 610 may include a circularly and rotationally symmetric object.

In some demonstrative embodiments, as shown in FIG. 6, the captured images 600 may be used in a detection of a cylindrical lens.

In some demonstrative embodiments, as shown in FIG. 6, object 610 may include radial elements, which maintain a certain frequency as a function of the radius of a captured image 600.

In some demonstrative embodiments, as shown in FIG. 6, a blur caused by the cylindrical lens may be determined based on the contrast of the imaged object 610 as a function of the radius and teta of object 610.

In some demonstrative embodiments, the use of captured images 610, which have different colors, may enable to analyze different focal planes at the same time, e.g., in and out of focus.

Referring back to FIG. 1, in some demonstrative embodiments, one or more other methods may be used to determine whether or not the lens includes a cylindrical lens, and/or to determine the axis of the lens, for example, if the lens includes the cylindrical lens.

In some demonstrative embodiments, application 160 may be configured to determine the cylindrical axis of the lens based on a comparison between one or more spatial elements of the object and one or more imaged spatial elements in the image, e.g., as described below.

In some demonstrative embodiments, application 160 may be configured to process a plurality of images corresponding to a plurality of rotations of the spatial elements in a plurality of angles.

In some demonstrative embodiments, application 160 may be configured to determine a plurality of magnifications between the one or more spatial elements of the object and the one or more imaged spatial elements corresponding to the plurality of rotations.

In some demonstrative embodiments, application 160 may be configured to determine the cylindrical axis, for example, based on the plurality of determined magnifications, e.g., as described below.

In one example, the spatial elements may include, for example, a cross-shaped element in the object and the imaged spatial elements may include an imaged cross-shaped element in the image.

According to this example, application 160 may be configured to process a plurality of images corresponding to a plurality of rotations of the cross-shaped element in a plurality of angles, to identify a co-aligned image in which the cross-shaped element and the imaged cross-shaped element are co-aligned, and to determine the cylindrical axis, for example, based on an angle of the imaged cross-shaped element, e.g., as described below.

Figure 7:
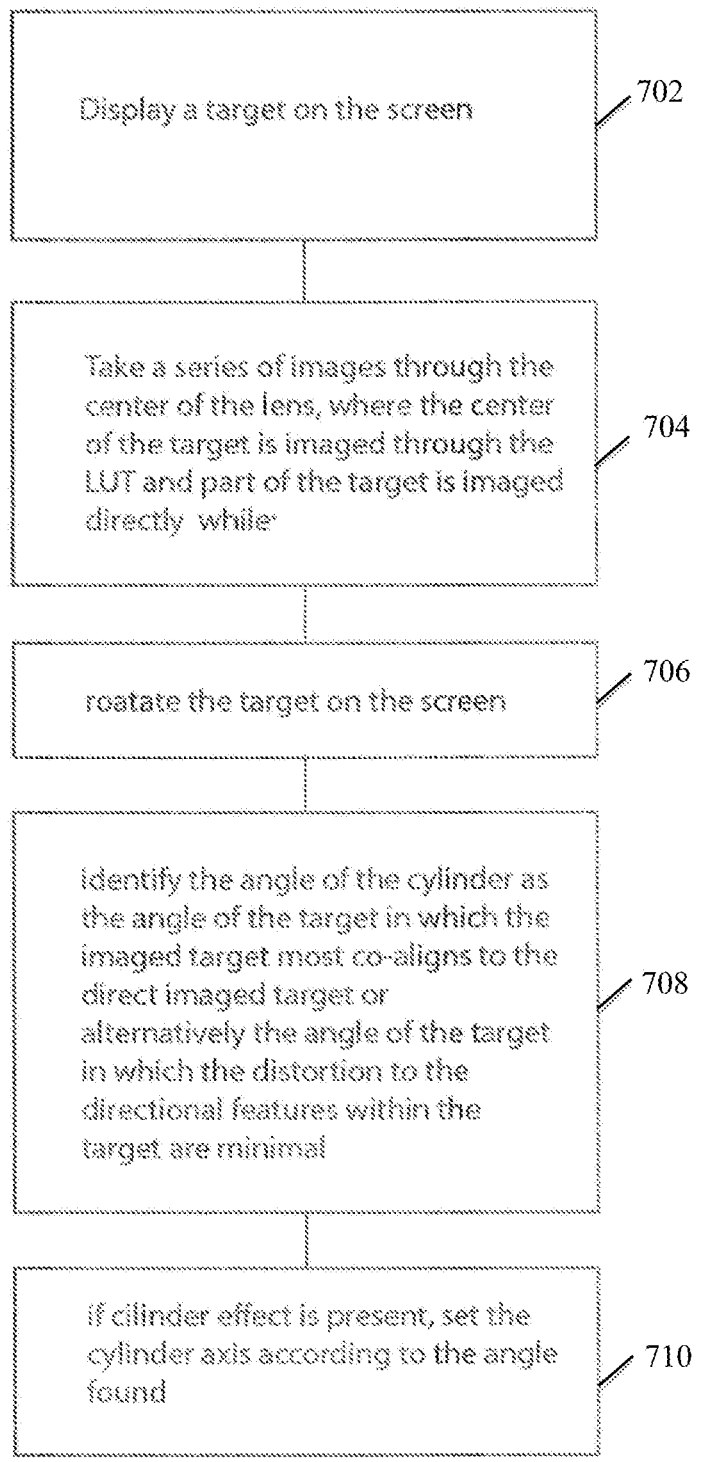
FIG. 7 is a schematic flow-chart illustration of a method of detecting a cylindrical lens and determining the axis of the cylindrical lens, in accordance with some demonstrative embodiments.

Reference is made to FIG. 7, which schematically illustrates a method of detecting a cylindrical lens and determining the axis of the cylindrical lens, in accordance with some demonstrative embodiments. For example, one or operations of the method of FIG. 7 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

As indicated at block 702, the method may include displaying an object on the display. For example, application 160 (FIG. 1) may cause display 130 (FIG. 1) to display the object, e.g., as described above.

As indicated at block 704, the method may include capturing a series of images through the lens, e.g., via the center of the lens, e.g., while rotating the object on the display. For example, application 160 (FIG. 1) may cause camera 118 (FIG. 1) to capture the images of the object displayed on display 130 (FIG. 1) via the center of the lens, for example, while causing the display 130 (FIG. 1) to display the object at the plurality of rotations, e.g., as described above.

As indicated at block 706, the method may include rotating the object on the display. For example, application 160 (FIG. 1) may cause display 130 (FIG. 1) to rotate the object, e.g., as described above.

As indicated at block 708, the method may include identifying an alignment angle at which the imaged object and the object most co-aligns, e.g., compared to other angles, and/or a minimal distortion angle of the imaged object, at which the distortion to directional features within the imaged object image are minimal. For example, application 160 (FIG. 1) may identify the co-alignment between the imaged object and the object, e.g., as described below.

As indicated at block 710, the method may include setting the cylindrical axis based on the alignment angle and/or the minimal distortion angle. For example, application 160 (FIG. 1) may determine the cylindrical axis based on the alignment angle, e.g., as described below.

Figure 8:
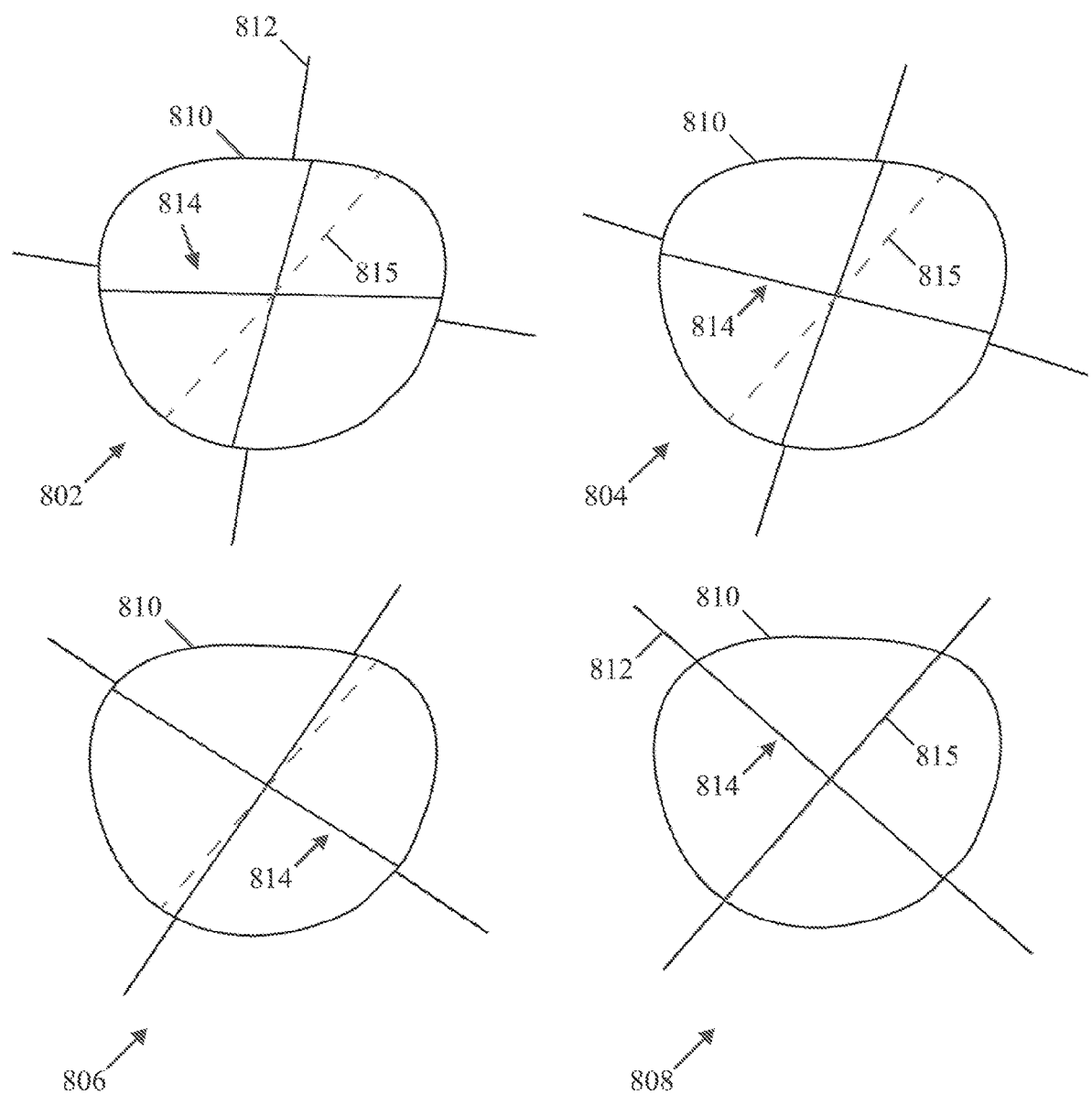
FIG. 8 is a schematic illustration of captured images useful in cylindrical axis identification, in accordance with some demonstrative embodiments.

Reference is made to FIG. 8, which schematically illustrates examples of captured images 802, 804, 806 and 808 useful in cylindrical axis identification of a lens 810, in accordance with some demonstrative embodiments.

In some demonstrative embodiments, images 802, 804, 806 and 808 may correspond to different rotations of spatial elements 812 of an object.

In some demonstrative embodiments, as shown in FIG. 8, cylindrical lens 810 may cause a geometrical magnification of spatial elements 812 along a cylindrical axis 815 of the cylindrical lens 810.

In some demonstrative embodiments, as shown in FIG. 8, the magnification may be between spatial elements 812 and imaged spatial elements 814 of the object, e.g., as may be captured via lens 810.

In some demonstrative embodiments, as shown in FIG. 8, spatial elements 812 and imaged spatial elements 814 may not be co-aligned in images 802, 804 and 806.

In some demonstrative embodiments, as shown in FIG. 8, spatial elements 812 and imaged spatial elements 814 may co-align in image 808.

In some demonstrative embodiments, as shown in FIG. 8, in image 808 spatial elements 812, imaged spatial elements 814 and cylindrical axis 815 may co-align. Accordingly, cylindrical axis 815 may be determined as the rotation of spatial elements 812 in image 808.

Referring back to FIG. 1, in some demonstrative embodiments, application 160 may be configured to determine the cylindrical power of the lens, for example, based on the cylindrical axis of the lens.

In some demonstrative embodiments, application 160 may use the detection of the cylindrical lens and the axis of cylindrical lens, e.g., as described above with reference to FIG. 5, 6, 7 and/or 8, for example, to determine a cylindrical power of the lens, e.g., as described below.

In some demonstrative embodiments, application 160 may be configured to determine a first power of the lens at the cylindrical axis.

In some demonstrative embodiments, application 160 may be configured to determine a second power of the lens at a perpendicular axis, which is perpendicular to the cylindrical axis.

In some demonstrative embodiments, application 160 may be configured to determine the cylindrical power of the lens, for example, based on the first and second powers, e.g., as described below.

Figure 9:
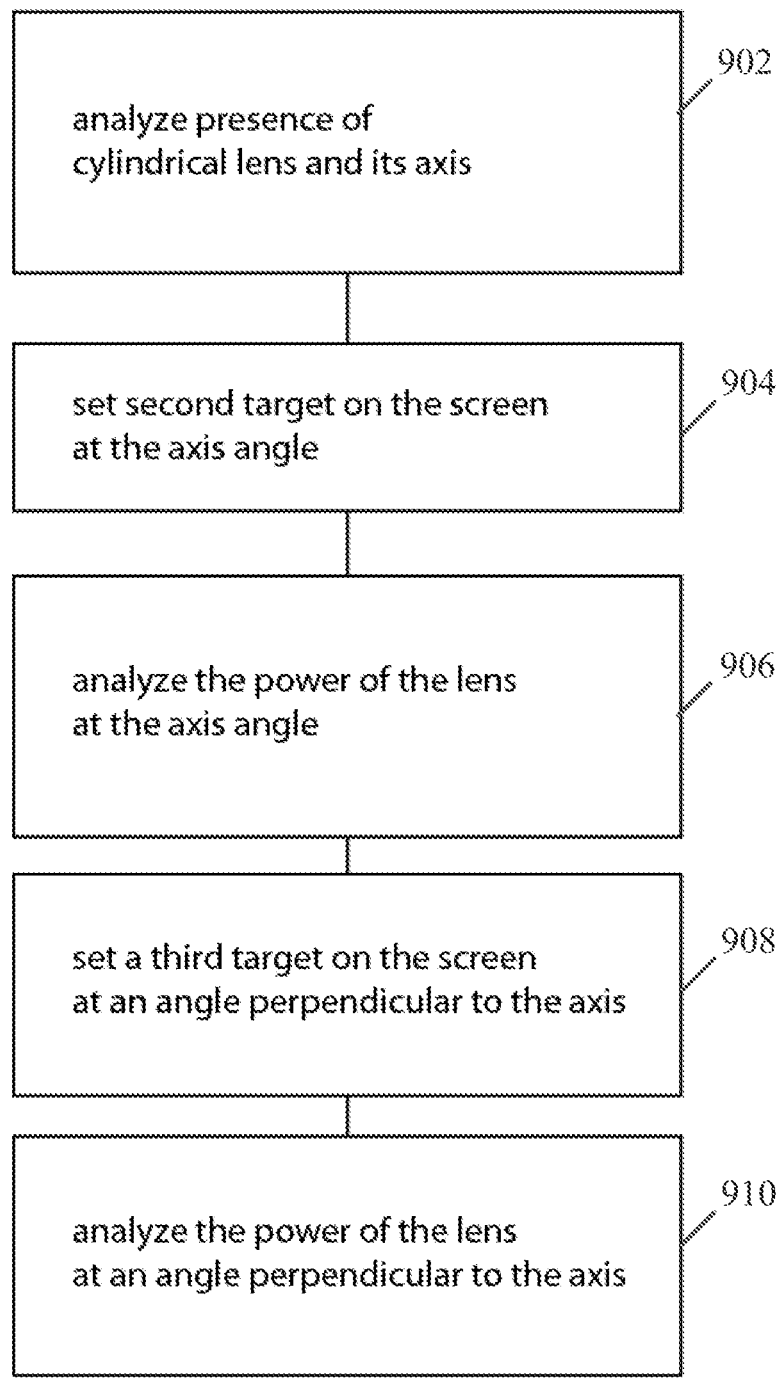
FIG. 9 is a schematic flow-chart illustration of a method of determining a power of a lens, in accordance with some demonstrative embodiments.

Reference is made to FIG. 9, which schematically illustrates a method of determining a cylindrical power of a lens, in accordance with some demonstrative embodiments. For example, one or operations of the method of FIG. 9 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

As indicated at block 902, the method may include detecting a cylindrical lens and an axis of the lens, for example, using a first displayed object, for example, according to one or more operations described above with reference to FIGS. 5, 6, 7, and/or 8. For example, application 160 (FIG. 1) may determine the cylindrical axis 816 (FIG. 8) of lens 810 (FIG. 8), e.g., as descried above.

As indicated at block 904, the method may include displaying a second object on the display at a first angle corresponding to the cylindrical axis of the lens. For example, application 160 (FIG. 1) may cause display 130 (FIG. 1) to display the second object at an angle corresponding to the cylindrical axis of the lens, e.g., as determined according to one or more operations described above with reference to FIGS. 5, 6, 7, and/or 8.

As indicated at block 906, the method may include analyzing the spherical power of the lens at the cylindrical axis when capturing the second image. For example, application 160 (FIG. 1) may determine the first power of the lens at the cylindrical axis, e.g., as described above.

In some demonstrative embodiments, analyzing the spherical power of the lens when displaying the second object may include, for example, one or more operations described above with reference to FIG. 4.

As indicated at block 908, the method may include displaying a third object on the display at a second angle perpendicular to the cylindrical axis of the lens. For example, application 160 (FIG. 1) may cause display 130

(FIG. 1) to display the third object at the angle perpendicular to the cylindrical axis of the lens.

As indicated at block 910, the method may include analyzing the spherical power of the lens at the perpendicular angle when capturing the third image. For example, application 160 (FIG. 1) may determine the second power of the lens at the perpendicular angle, e.g., as described above.

In some demonstrative embodiments, analyzing the spherical power of the lens when displaying the third object may include, for example, one or more operations described above with reference to FIG. 4.

Referring back to FIG. 1, in some demonstrative embodiments, application 160 may be configured to determine a sign of the lens, e.g., to identify a converging lens or diverging lens.

In some demonstrative embodiments, application 160 may be configured to determine the sign of the lens for example, based on at least one image captured via the lens, e.g., as described below.

In some demonstrative embodiments, application 160 may be configured to cause camera 118 to capture a plurality of images of the object via the lens, for example, while the eyeglasses are moved in a particular direction. In one example, application 160 may be configured to instruct the user to move the eyeglasses.

In some demonstrative embodiments, application 160 may be configured to identify a movement pattern in the plurality of captured images.

In some demonstrative embodiments, application 160 may be configured to determine the sign of the lens based on the movement pattern, e.g., as described below.

Figure 10:
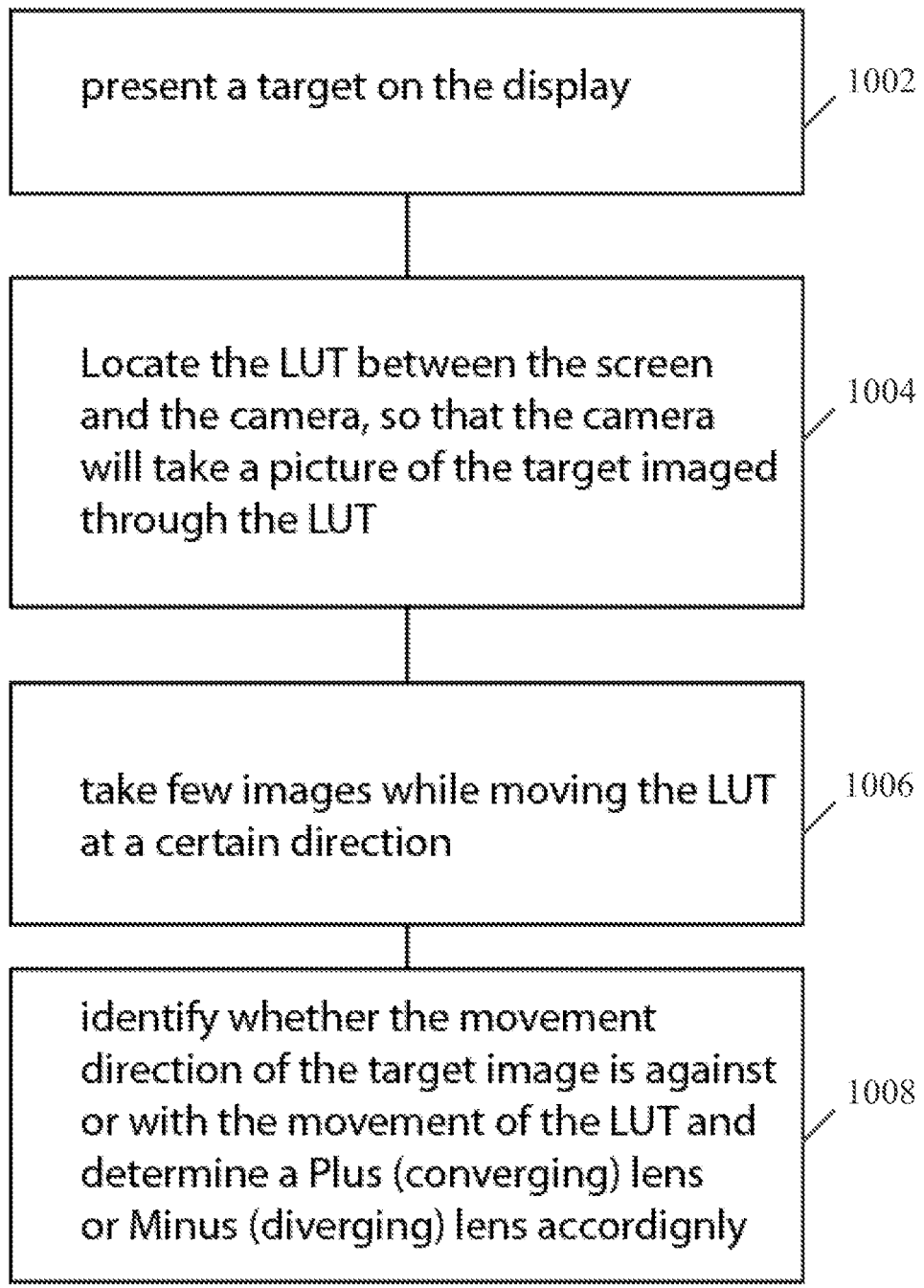
FIG. 10 is a schematic flow-chart illustration of a method of determining a sign of a lens, in accordance with some demonstrative embodiments.

Reference is made to FIG. 10, which schematically illustrates a method of determining a sign of a lens, in accordance with some demonstrative embodiments. For example, one or operations of the method of FIG. 10 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

As indicated at block 1002, the method may include displaying an object on the display. For example, application 160 (FIG. 1) may cause display 130 (FIG. 1) to display the object, e.g., as described above.

As indicated at block 1004, the method may include locating the lens between the display and the camera and capturing an image of the object via the lens. For example, application 160 (FIG. 1) may instruct the user of the eyeglasses to capture the image of the object via the lens, e.g., as described above.

As indicated at block 1006, the method may include capturing a series of images while moving the lens in a predefined direction. For example, application 160 (FIG. 1) may cause camera 118 (FIG. 1) to capture the series of images, while instructing the user to move the lens in a predefined direction, e.g., as described above.

As indicated at block 1008, the method may include identifying the sign of the lens based on the movement direction of the imaged object image in the captured image. For example, application 160 (FIG. 1) may determine the sign of the lens based on the movement pattern, e.g., as described below.

In one example, the method may include determining the lens includes a converging lens, e.g., a Plus lens, for example, if the direction of movement of the imaged object is opposite to the predefined direction.

In another example, the method may include determining the lens includes a diverging lens, e.g., a Minus lens, for example, if the direction of movement of the imaged object is the same as the predefined direction.

Referring back to FIG. 1, in some demonstrative embodiments, application 160 may be configured to determine a pupillary distance between a pair of lenses, e.g., a first lens and a second lens, which are assembled into the frame of the eyeglasses, e.g., as described below.

In some demonstrative embodiments, application 160 may be configured to determine the pupillary distance, for example, based on a distance between a first center of the first lens and a second center of the second lens, e.g., as described below.

In some demonstrative embodiments, application 160 may be configured to perform one or more operations to determine the pupillary distance, e.g., as described below.

In some demonstrative embodiments, application 160 may be configured to instruct the user to use camera 118 to capture a first image of the object without the lens.

In some demonstrative embodiments, application 160 may be configured to identify a second image captured via the lens, which co-aligns with the first image.

In some demonstrative embodiments, application 160 may be configured to determine a first location, e.g., when the second image is captured.

In some demonstrative embodiments, application 160 may be configured to identify a third image captured via the second lens, which co-aligns with the first image.

In some demonstrative embodiments, application 160 may be configured to determine a second location, e.g., when the third image is captured.

In some demonstrative embodiments, applications 160 may be configured to determine the pupillary distance based on the first and second locations, e.g., as described below.

Figure 11:
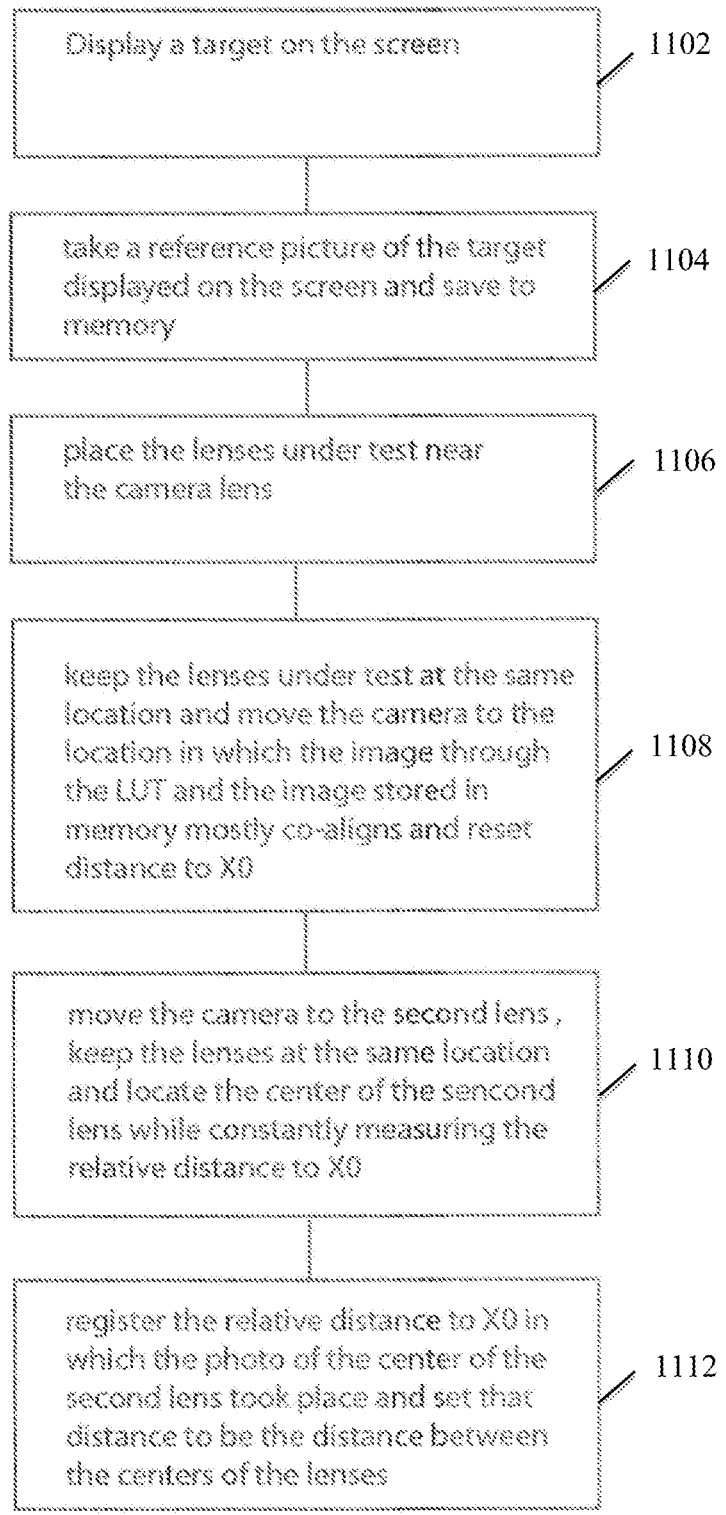
FIG. 11 is a schematic flow-chart illustration of a method of determining a pupillary distance between a pair of lenses of eyeglasses, in accordance with some demonstrative embodiments.

Reference is made to FIG. 11, which schematically illustrates a method of determining a pupillary distance between a pair of lenses of eyeglasses, in accordance with some demonstrative embodiments. For example, one or operations of the method of FIG. 11 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

As indicated at block 1102, the method may include displaying an object on a display. For example, application 160 (FIG. 1) may cause display 130 (FIG. 1) to display the object, e.g., as described above.

As indicated at block 1104, the method may include capturing a reference image of the object displayed on the display, e.g., without the lens. For example, application 160 (FIG. 1) may cause camera 118 (FIG. 1) to capture the image of the object, for example, not through the lens.

As indicated at block 1106, the method may include placing the lens near the camera lens. For example, application 160 (FIG. 1) may instruct the user to place the lens near the camera lens of camera 118 (FIG. 1).

As indicated at block 1108, the method may include moving the camera to a first location, at which an image of the object captured via the first lens and the reference image of the object are substantially co-aligned. For example, application 160 (FIG. 1) may instruct the user to move camera 118 (FIG. 1) to the location at which the reference image and the captured image via the first lens are co-aligned.

As indicated at block 1108, the method may include resetting a lateral distance to $x_0$ at the first location. For example, application 160 (FIG. 1) may reset the lateral distance at the first location.

As indicated at block 1110, the method may include moving the camera to a center of the second lens of the eyeglasses, and measuring the relative distance to the location x, while the frame remains at the same position. For example, application 160 (FIG. 1) may instruct the user to move the camera 118 (FIG. 1) to the center of the second lens of the eyeglasses, and application 160 may determine the relative distance from the location x to the location x0, while the frame remains at the same position.

As indicated at block 1112, the method may include capturing a second image of the object via the second lens at a second location, at which a captured image of the object via the second lens and the reference image of the object are substantially co-aligned. For example, application 160 (FIG. 1) may instruct the user to move camera 118 (FIG. 1) to the location at which the reference image and captured image via the second lens are co-aligned, e.g., as described above.

As indicated at block 1112, the method may include determining a relative distance between the location x0 and the second location, and setting the relative distance as the pupillary distance of the eyeglasses. For example, application 160 (FIG. 1) may determine the pupillary distance based on the distance between the two centers of the first and second lenses.

Figure 12:
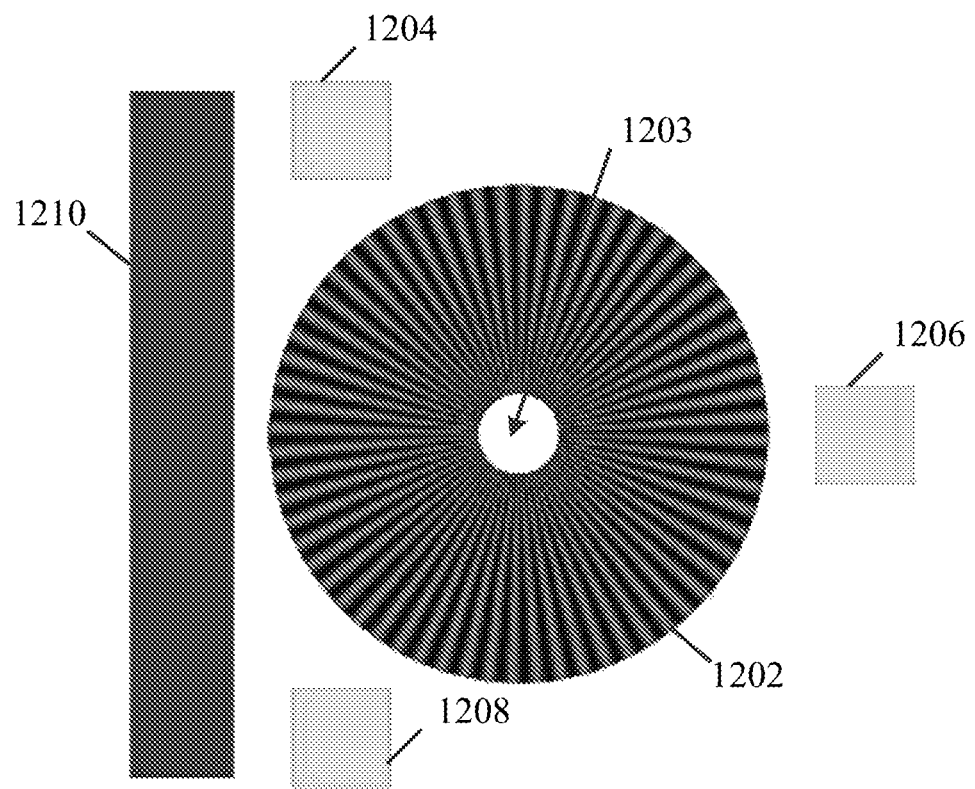
FIG. 12 is a schematic illustration of a graphical display of an object, in accordance with some demonstrative embodiments.

Reference is made to FIG. 12, which schematically illustrates a graphical display 1200, in accordance with some demonstrative embodiments.

In some demonstrative embodiments, application 160 (FIG. 1) may be configured to cause display 130 (FIG. 1) to display graphical display 1200.

In some demonstrative embodiments, as shown in FIG. 12, graphical display 1200 may include an object 1202, e.g., a sinusoidal roseta, and one or more calibration objects 1204, 1206, 1208, and/or 1210.

In some demonstrative embodiments, a method to determine a sharpest image from a set of captured images on a display, e.g., display 130 (FIG. 1), may include determining the sharpest image based on a sharpness criterion, a blur criterion, a contrast criterion and/or an aliasing criterion, in which an image density of pixels of the display closely matches a density of the sensor pixels, e.g., if a captured image is in focus.

In some demonstrative embodiments, the method to determine the sharpest image may be applied in a directional manner.

Some demonstrative embodiments may enable to apply one or more methods to identify the sharpest image.

In some demonstrative embodiments, a contrast method to determine sharpest image may be performed using an imaged object of object 1202.

In some demonstrative embodiments, as shown in FIG. 12, a frequency of one or more features of the imaged object of object 1202 may be linearly proportional to the radius of the imaged object. Accordingly, application 160 (FIG. 1) may be configured to select the radius according to the distance in which the imaged object was captured, and may be able to analyze a contrast along one or more angles.

For example, the contrast may be compared between a plurality of different magnifications, e.g., corresponding to a plurality of different distances from the imaged object, while analyzing the same spatial frequencies of the imaged object.

In some demonstrative embodiments, as shown in FIG. 12, the one or more calibration objects 1204, 1206, 1208, and/or 1210 may be used, e.g., by application 160 (FIG. 1), as "known size" elements, for example, to determine a distance between an image capturing device, e.g., camera 118 (FIG. 1), and object 1202.

In some demonstrative embodiments, as shown in FIG. 12, calibration element 1210 may include, for example, a rectangle of a first color, e.g., blue, and/or calibration elements 1204, 1206 and 1208 may include, for example, three cubes of a second color, e.g., green, for example, for orientation features.

In some demonstrative embodiments, as shown in FIG. 12, object 1202 may include an inner circle 1203, which is mostly close to the center of region of object 1202.

In some demonstrative embodiments, inner circle 1203 may be used, e.g., by application 160 (FIG. 1) as a calibration element.

In some demonstrative embodiments, different colors, e.g., for the one or more elements of FIG. 12, may be used to enhance chromatic effects of the lens of camera 118 (FIG. 1).

In some demonstrative embodiments, using the different colors may enable to separate between the one or more elements, for example, by image processing, e.g., at application 160 (FIG. 1).

In some demonstrative embodiments, application 160 (FIG. 1) may be configured to use the known size elements, e.g., calibration elements 1204, 1206, 1208, and/or 1210, at a known predetermined size at different locations with respect to object 1202, for example, to analyze a perspective deformation, which may result, for example, from misalignment of the plane of object 1202 and the plane of the sensor of the camera 118 (FIG. 1), and/or to consider and/or correct the perspective deformation.

Figure 13:
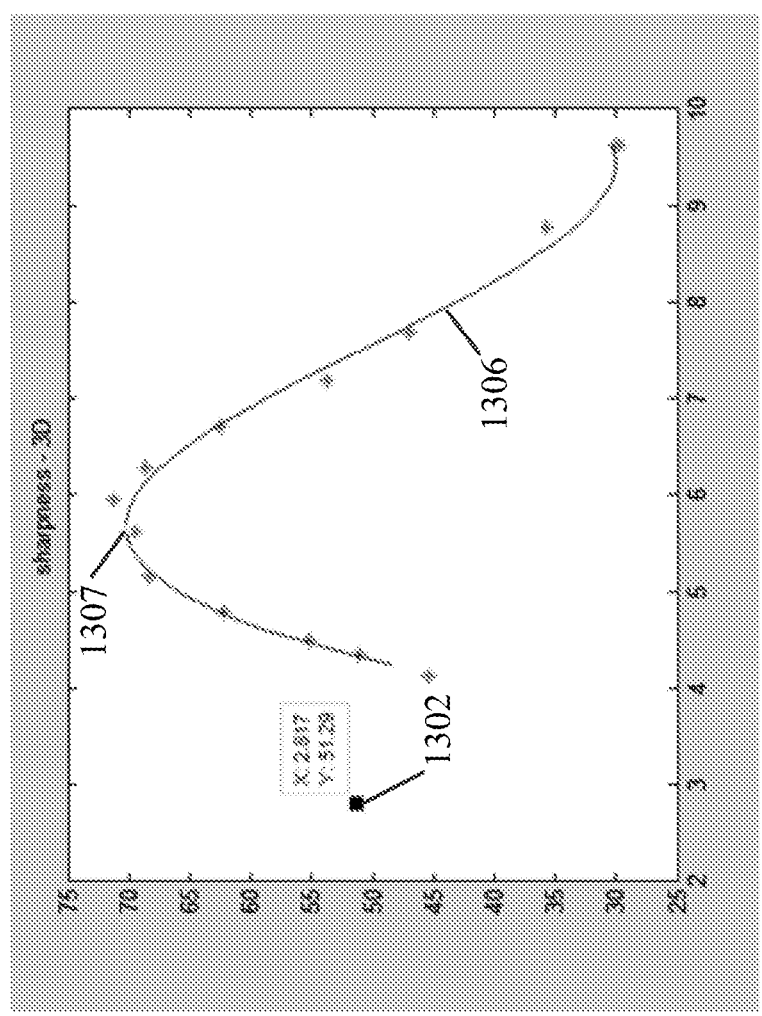
FIG. 13 is a schematic illustration of a graph depicting a distance of an object versus contrast, in accordance with some demonstrative embodiments.

Reference is made to FIG. 13, which schematically illustrates a graph depicting a distance (1/m) of an object versus contrast, in accordance with some demonstrative embodiments.

In some demonstrative embodiments, as shown in FIG. 13, the asterisks in the graph may identify a distance (1/m), e.g., over the X-axis, at which an image of an object was captured, and a contrast value corresponding to a contrast of the captured image, e.g., over the Y-axis.

In one example, the distance may be determined, e.g., by application 160 (FIG. 1) for example, based on known size elements, e.g., elements 1203, 1204, 1206, 1208 and/or 1210 (FIG. 12).

In some demonstrative embodiments, as shown in FIG. 13, a black cube marker 1302 may depict a reference image captured via the lens.

In some demonstrative embodiments, as shown in FIG. 13, a line 1306 may include a fitting model correlation, e.g., to identify a sharpest location in a precise manner, which is depicted by cross 1307.

In one example, the reference image may be captured at a first distance of 355 mm, which may be equal to a first diopter value of 2.817 Diopters. According to this example, the sharpest image may be located at a second distance corresponding to a second diopter value of 5.8 Diopters, e.g., marked by the cross 1307. Accordingly, application 160 (FIG. 1) may determine the spherical power of the lens to include the difference between the first and second diopters values, e.g., 2.8-5.8=−3 Diopters.

In some demonstrative embodiments, application 160 (FIG. 1) may be configured to determine which objects to display on display 130 (FIG. 1).

Referring back to FIG. 1, in some demonstrative embodiments, application 160 may be configured to calibrate display 130.

In some demonstrative embodiments, a size of the display 130 may be known.

In some demonstrative embodiments, the display size of the display 130 may be known, for example, if the display is integrated within a portable device, e.g., a Smartphone or a tablet, e.g., based on the model of the device.

In some demonstrative embodiments, a calibration of the display size of the display may be performed.

Figure 14:
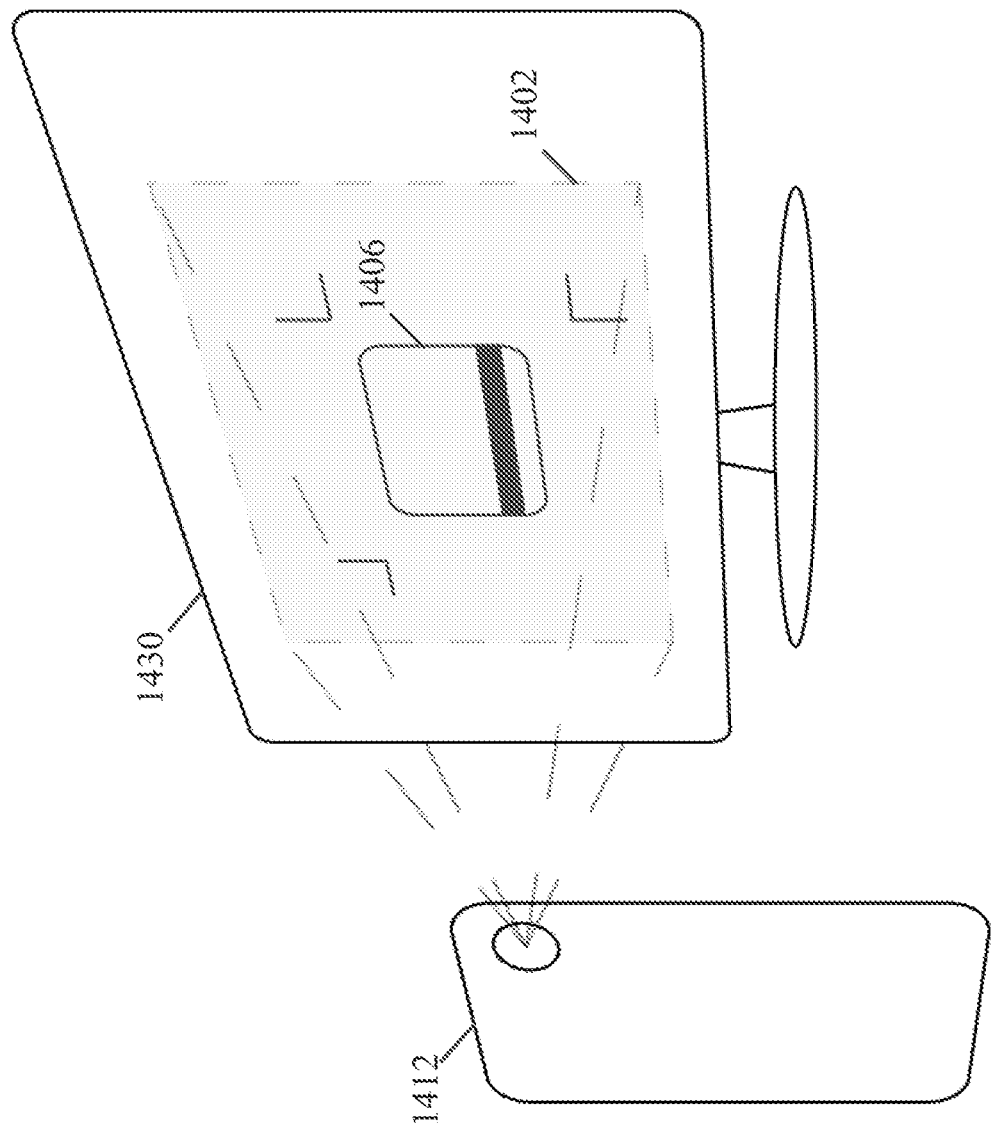
FIG. 14 is a schematic illustration of a system to calibrate a display size of a display device, in accordance with some demonstrative embodiments.

Reference is made to FIG. 14, which schematically illustrates a system 1400 to calibrate a display size 1402 of a display device 1430, in accordance with some demonstrative embodiments. For example, display 1430 may perform the functionality of display 130 (FIG. 1).

In some demonstrative embodiments, application 160 (FIG. 1) may perform a calibration process and/or procedure, for example, to calibrate the display size 1402.

In some demonstrative embodiments, a scale to one or more features of known size over the display may be applied. The scaling may be automated by recognizing one or more known size features of the object and by recognizing one or more features of the frame, e.g., using image processing.

In some demonstrative embodiments, the calibration process may include adjusting a size of a feature on the display to a known size object 1406, for example, a magnetic card, a CD or any other known size object.

In some demonstrative embodiments, the calibration procedure may include capturing by an image capturing device 1412, e.g., camera 118 (FIG. 1), an image including a predefined object displayed on the display 1430, and the known size object 1406 placed upon the display 1430.

In some demonstrative embodiments, a scaling procedure may be configured to match the size of the predefined object into absolute dimensions, for example, to match the size of the predefined object to the size of known size object 1406.

In some demonstrative embodiments, the scaling procedure may include, for example, detecting one or more features of the predefined object, e.g., using image processing, and one or more features of the known size object 1406.

In some demonstrative embodiments, the scaling procedure may include, for example, measuring at least a length of the predefined object as captured by a camera of the device 1412, and comparing the length of the predefined object to a length of the known size object 1406.

In some demonstrative embodiments, a size of the predefined object may be of any shape and size and may not have to match a size and/or the one or more features of the known size object.

In some demonstrative embodiments, a manual adjustment of the features of the predefined object may be performed to match the size or other features of the known size object 1406, while a change of the manual adjustment is recorded and set for a required scale of the display 1430.

In some demonstrative embodiments, one or more additional or alternative methods to scale the display may be performed.

In one example, a method may include capturing an image of the display 1430 from a predefined distance, while a predefined object is displayed on the display, for example, without using the known size object.

In some demonstrative embodiments, a scale of the image to the plane of the display can be deduced, e.g., as follows:

$$h \cong \frac{efl}{pitch} * \frac{camera\_screen\_distance}{h'\_pixel\_estimated} \quad (6)$$

wherein h denotes an absolute size of the predefined object feature as displayed on the display.

In some demonstrative embodiments, determining the scale may be performed using suitable methods, for example, if measuring the real size of the predefined object displayed on the display, to match a predefined size.

Figure 15:
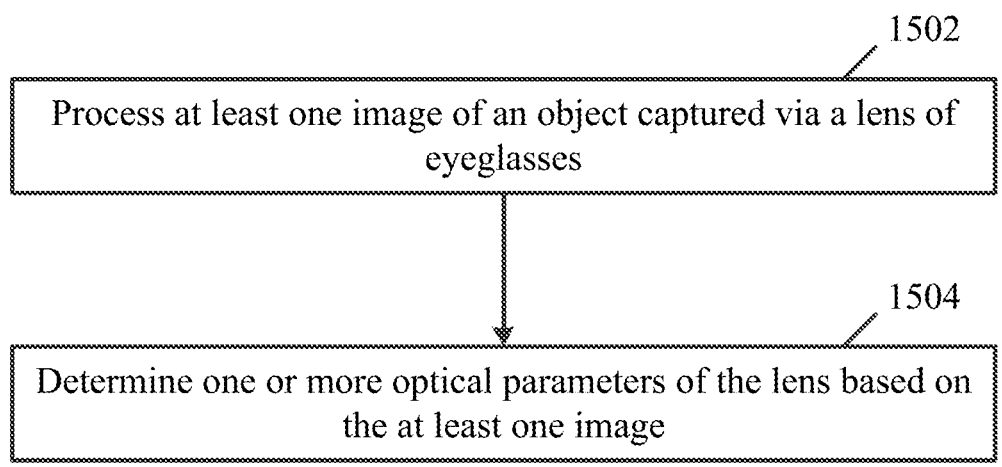
FIG. 15 is a schematic flow-chart illustration of a method of determining one or more optical parameters of a lens, in accordance with some demonstrative embodiments.

Reference is made to FIG. 15, which schematically illustrates a method of determining one or more optical parameters of a lens, in accordance with some demonstrative embodiments. For example, one or operations of the method of FIG. 15 may be performed by a system, e.g., system 100 (FIG. 1); a mobile device, e.g., device 102 (FIG. 1); a server, e.g., server 170 (FIG. 1); a display, e.g., display 130 (FIG. 1); and/or an application, e.g., application 160 (FIG. 1).

As indicated at block 1502, the method may include processing at least one image of an object captured via the lens. For example, application 160 (FIG. 1) may process the at least one image captured via the lens of the object displayed over display 130 (FIG. 1), e.g., as described above.

As indicated at block 1504, the method may include determining the one or more optical parameters of the lens based on said at least one image. For example, application 160 (FIG. 1) may determine the one or more optical parameters of the lens based on the at least one image.

Referring back to FIG. 1, in some demonstrative embodiments, application 160 may be configured to determine the one or more optical parameters of a lens, for example, even without using display 130. For example, application 160 may be configured to determine a cylindrical power, and/or a cylinder angle and/or a spherical power of the lens, for example, even without using display 130, e.g., as described below.

In some demonstrative embodiments, application 160 may be configured to determine the one or more optical parameters of a lens, for example, even without displaying an image on display 130.

In some demonstrative embodiments, application 160 may be configured to determine the one or more optical parameters of a lens, for example, based on a captured image of an object having a known size, e.g., as described below.

In some demonstrative embodiments, lens parameters such as sphere power, cylinder power and/or cylinder angle may be found, for example, by using a camera or a Smartphone device and an object of a known size.

In some demonstrative embodiments, by taking an image of the object of known size through the lens, the lens parameters may be found.

In some demonstrative embodiments, the object of known size may include, for example, a coin having a known size, an Iris of the eye or a calibrated iris diameter of the eye, and/or any other object or element.

In some demonstrative embodiments, using the known size object may allow determining the one or more optical parameters of a lens, for example, even without using a screen to display an object, and/or even without calibration prior to measurement of the lens parameters.

In some demonstrative embodiments, the lens power and/or cylinder parameters may be deduced from a deformation of the observed image of the known size object through the tested lens relative to an image of the known size object, which may be observed directly without the test lens.

In some demonstrative embodiments, spectacle glasses parameters, e.g., a sphere power, a cylinder power and/or a cylinder angle, may be determined, for example, using a camera or a Smartphone device, e.g., even without using an external object of known size.

In some demonstrative embodiments, by taking an image of an eye of a wearer of the spectacles, it may be possible to analyze a change in an Iris size of the Iris of the wearer resulting from the spectacle glasses. For example, an image of the Iris with and without the spectacles may be compared and analyzed, e.g., to determine the spectacle glasses parameters.

In some demonstrative embodiments, if needed, an iris absolute size may be calibrated, for example, using a known size object, e.g., a coin or a credit card.

Figure 16:
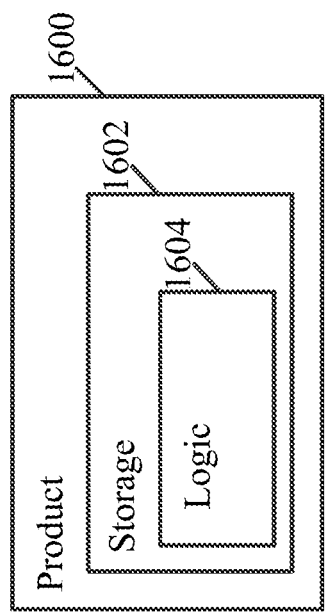
FIG. 16 is a schematic illustration of a product, in accordance with some demonstrative embodiments.

Reference is made to FIG. 16, which schematically illustrates a product of manufacture 1600, in accordance with some demonstrative embodiments. Product 1600 may include one or more tangible computer-readable non-transitory storage media 1602, which may include computer-executable instructions, e.g., implemented by logic 1604, operable to, when executed by at least one computer processor, enable the at least one computer processor to implement one or more operations at device 102 (FIG. 1), server 170 (FIG. 1), display 130 (FIG. 1), and/or application 160 (FIG. 1), and/or to perform, trigger and/or implement one or more operations, communications and/or functionalities according to FIGS. 1-15, and/or one or more operations described herein. The phrase "non-transitory machine-readable medium" is directed to include all computer-readable media, with the sole exception being a transitory propagating signal.

In some demonstrative embodiments, product 1600 and/or machine-readable storage medium 1602 may include one or more types of computer-readable storage media capable of storing data, including volatile memory, non-volatile memory, removable or non-removable memory, erasable or non-erasable memory, writeable or re-writeable memory, and the like. For example, machine-readable storage medium 1602 may include, RAM, DRAM, Double-Data-Rate DRAM (DDR-DRAM), SDRAM, static RAM (SRAM), ROM, programmable ROM (PROM), erasable programmable ROM (EPROM), electrically erasable programmable ROM (EEPROM), Compact Disk ROM (CD-ROM), Compact Disk Recordable (CD-R), Compact Disk Rewriteable (CD-RW), flash memory (e.g., NOR or NAND flash memory), content addressable memory (CAM), polymer memory, phase-change memory, ferroelectric memory, silicon-oxide-nitride-oxide-silicon (SONOS) memory, a disk, a floppy disk, a hard drive, an optical disk, a magnetic disk, a card, a magnetic card, an optical card, a tape, a cassette, and the like. The computer-readable storage media may include any suitable media involved with downloading or transferring a computer program from a remote computer to a requesting computer carried by data signals embodied in a carrier wave or other propagation medium through a communication link, e.g., a modem, radio or network connection.

In some demonstrative embodiments, logic 1604 may include instructions, data, and/or code, which, if executed by a machine, may cause the machine to perform a method, process and/or operations as described herein. The machine may include, for example, any suitable processing platform, computing platform, computing device, processing device, computing system, processing system, computer, processor, or the like, and may be implemented using any suitable combination of hardware, software, firmware, and the like.

In some demonstrative embodiments, logic 1604 may include, or may be implemented as, software, a software module, an application, a program, a subroutine, instructions, an instruction set, computing code, words, values, symbols, and the like. The instructions may include any suitable type of code, such as source code, compiled code, interpreted code, executable code, static code, dynamic code, and the like. The instructions may be implemented according to a predefined computer language, manner or syntax, for instructing a processor to perform a certain function. The instructions may be implemented using any suitable high-level, low-level, object-oriented, visual, compiled and/or interpreted programming language, such as C, C++, Java, BASIC, Matlab, Pascal, Visual BASIC, assembly language, machine code, and the like.

EXAMPLES

The following examples pertain to further embodiments.

Example 1 includes a product comprising one or more tangible computer-readable non-transitory storage media comprising computer-executable instructions operable to, when executed by at least one computer processor, enable the at least one computer processor to implement operations of determining one or more optical parameters of a lens of eyeglasses, the operations comprising processing at least one image of an object captured via the lens; and determining the one or more optical parameters of the lens based on the at least one image.

Example 2 includes the subject matter of Example 1, and optionally, wherein the operations comprise determining a power of the lens based on autofocus information of an image-capturing device, when the image is captured.

Example 3 includes the subject matter of Example 2, and optionally, wherein the operations comprise processing a first image of the object captured via the lens at a first distance between the object and the image-capturing device, and a second image of the object captured without the lens at a second distance between the object and the image-capturing device, and determining the power of the lens based on the first and second distances, first autofocus information of the image-capturing device when the first image is captured, and second autofocus information of the image-capturing device when the second image is captured.

Example 4 includes the subject matter of any one of Examples 1-3, and optionally, wherein the operations comprise determining a power of the lens based on a sharpness parameter of a sharpness of one or more spatial frequencies in the image.

Example 5 includes the subject matter of Example 4, and optionally, wherein the operations comprise processing a plurality of images of the object captured not via the lens at a respective plurality of distances between the object and an image-capturing device, determining a sharpest image of the plurality of images comprising the one or more spatial frequencies, and determining the power of the lens based on a first distance between the object and the image-capturing device, when the sharpest image is captured and a second distance between the object and the image-capturing device, when the at least one image is captured via the lens.

Example 6 includes the subject matter of any one of Examples 1-5, and optionally, wherein the operations comprise determining the one or more optical parameters of the lens based at least on one or more dimensions of the object.

Example 7 includes the subject matter of Example 6, and optionally, wherein the operations comprise determining one or more imaged dimensions of the object in the image, and determining the one or more optical parameters of the lens based at least on a magnification between the one or more dimensions and the one or more imaged dimensions.

Example 8 includes the subject matter of any one of Examples 1-7, and optionally, wherein the operations comprise identifying an existence of a cylindrical axis of the lens based on one or more visual affects of one or more spatial frequencies in the image.

Example 9 includes the subject matter of Example 8, and optionally, wherein the operations comprise determining the cylindrical axis based at least on an angle of a non-symmetrical blur of the one or more spatial frequencies.

Example 10 includes the subject matter of Example 8 or 9, and optionally, wherein the operations comprise determining existence of the cylindrical axis based at least on an angle of a sharpest portion of the spatial frequencies.

Example 11 includes the subject matter of any one of Examples 1-10, and optionally, wherein the operations comprise determining a cylindrical axis of the lens based on a comparison between one or more spatial elements of the object and one or more imaged spatial elements in the image.

Example 12 includes the subject matter of Example 11, and optionally, wherein the operations comprise processing a plurality of images corresponding to a plurality of rotations of the spatial elements in a plurality of angles, determining a plurality of magnifications between the one or more spatial elements of the object and the one or more imaged spatial elements, and determining the cylindrical axis based on the magnifications.

Example 13 includes the subject matter of any one of Examples 1-12, and optionally, wherein the operations comprise determining the one or more optical parameters of the lens based on a distance between the object and an image-capturing device, when the image is captured.

Example 14 includes the subject matter of Example 13, and optionally, wherein the operations comprise determining the distance between the object and the image-capturing device, based on acceleration information indicating an acceleration of the image capturing device.

Example 15 includes the subject matter of any one of Examples 1-14, and optionally, wherein the operations comprise determining a cylindrical power of the lens based on a cylindrical axis of the lens.

Example 16 includes the subject matter of Example 15, and optionally, wherein the operations comprise determining a first power of the lens at the cylindrical axis, determining a second power of the lens at a perpendicular axis, which is perpendicular to the cylindrical axis, and determining the cylindrical power based on the first and second powers.

Example 17 includes the subject matter of any one of Examples 1-16, and optionally, wherein the operations comprise determining a pupillary distance between the lens and an other lens of the eyeglasses based on a distance between a first center of the lens and a second center of the other lens.

Example 18 includes the subject matter of Example 17, and optionally, wherein the operations comprise processing a first image of the object, which is captured without the lens; identifying a second image captured via the lens, which co-aligns with the first image; determining a first location when the second image is captured; identifying a third image captured via the other lens, which co-aligns with the first image; determining a second location when the third image is captured; and determining the pupillary distance based on the first and second locations.

Example 19 includes the subject matter of any one of Examples 1-18, and optionally, wherein the operations comprise determining a sign of the lens based on the at least one image.

Example 20 includes the subject matter of Example 19, and optionally, wherein the operations comprise identifying a movement pattern in a plurality of captured images, the plurality of captured images comprising images of the object captured via the lens when the lens is moved in a particular direction, and determining the sign of the lens based on the movement pattern.

Example 21 includes the subject matter of any one of Examples 1-20, and optionally, wherein the operations comprise determining the one or more optical parameters of the lens based on a single frame including the at least one image of the object via the lens.

Example 22 includes the subject matter of any one of Examples 1-21, and optionally, wherein the one or more optical parameters of the lens comprise one or more parameters selected form the group consisting of a spherical power, a cylindrical power, a cylindrical axis, and a pupillary distance between lenses of the eyeglasses.

Example 23 includes the subject matter of any one of Examples 1-22, and optionally, wherein the operations comprise causing a display device to display the object.

Example 24 includes the subject matter of Example 23, and optionally, wherein the operations comprise calibrating a display size of the object on the display device.

Example 25 includes the subject matter of any one of Examples 1-24, and optionally, wherein the object comprises an object having one or more known dimensions, the operations comprising determining the optical parameters based on the dimensions.

Example 26 includes the subject matter of any one of Examples 1-25, and optionally, wherein the object comprises a circularly symmetric or rotationally symmetric object.

Example 27 includes the subject matter of any one of Examples 1-26, and optionally, wherein the operations comprise causing an image capturing device to capture the image of the object.

Example 28 includes a mobile device configured to determine one or more optical parameters of a lens of eyeglasses, the mobile device comprising a camera to capture at least one image of an object via the lens; and a lensometer module to determine the one or more optical parameters of the lens based on the at least one image.

Example 29 includes the subject matter of Example 28, and optionally, wherein the mobile device is configured to determine a power of the lens based on autofocus information of the camera, when the image is captured.

Example 30 includes the subject matter of Example 29, and optionally, wherein the mobile device is configured to process a first image of the object captured via the lens at a first distance between the object and the camera, and a second image of the object captured without the lens at a second distance between the object and the camera, and to determine the power of the lens based on the first and second distances, first autofocus information of the camera when the first image is captured, and second autofocus information of the camera when the second image is captured.

Example 31 includes the subject matter of any one of Examples 28-30, and optionally, wherein the mobile device is configured to determine a power of the lens based on a sharpness parameter of a sharpness of one or more spatial frequencies in the image.

Example 32 includes the subject matter of Example 31, and optionally, wherein the mobile device is configured to process a plurality of images of the object captured not via the lens at a respective plurality of distances between the object and the camera, to determine a sharpest image of the plurality of images comprising the one or more spatial frequencies, and to determine the power of the lens based on a first distance between the object and the camera, when the sharpest image is captured and a second distance between the object and the camera, when the at least one image is captured via the lens.

Example 33 includes the subject matter of any one of Examples 28-32, and optionally, wherein the mobile device is configured to determine the one or more optical parameters of the lens based at least on one or more dimensions of the object.

Example 34 includes the subject matter of Example 33, and optionally, wherein the mobile device is configured to determine one or more imaged dimensions of the object in the image, and to determine the one or more optical parameters of the lens based at least on a magnification between the one or more dimensions and the one or more imaged dimensions.

Example 35 includes the subject matter of any one of Examples 28-34, and optionally, wherein the mobile device is configured to identify an existence of a cylindrical axis of the lens based on one or more visual affects of one or more spatial frequencies in the image.

Example 36 includes the subject matter of Example 35, and optionally, wherein the mobile device is configured to determine the cylindrical axis based at least on an angle of a non-symmetrical blur of the one or more spatial frequencies.

Example 37 includes the subject matter of Example 35 or 36, and optionally, wherein the mobile device is configured to determine existence of the cylindrical axis based at least on an angle of a sharpest portion of the spatial frequencies.

Example 38 includes the subject matter of any one of Examples 28-37, and optionally, wherein the mobile device is configured to determine a cylindrical axis of the lens based on a comparison between one or more spatial elements of the object and one or more imaged spatial elements in the image.

Example 39 includes the subject matter of Example 38, and optionally, wherein the mobile device is configured to process a plurality of images corresponding to a plurality of rotations of the spatial elements in a plurality of angles, to determine a plurality of magnifications between the one or more spatial elements of the object and the one or more imaged spatial elements, and to determine the cylindrical axis based on the magnifications.

Example 40 includes the subject matter of any one of Examples 28-39, and optionally, wherein the mobile device is configured to determine the one or more optical parameters of the lens based on a distance between the object and the camera, when the image is captured.

Example 41 includes the subject matter of Example 40, and optionally, wherein the mobile device is configured to determine the distance between the object and the camera, based on acceleration information indicating an acceleration of the camera device.

Example 42 includes the subject matter of any one of Examples 28-41, and optionally, wherein the mobile device is configured to determine a cylindrical power of the lens based on a cylindrical axis of the lens.

Example 43 includes the subject matter of Example 42, and optionally, wherein the mobile device is configured to determine a first power of the lens at the cylindrical axis, to determine a second power of the lens at a perpendicular axis, which is perpendicular to the cylindrical axis, and to determine the cylindrical power based on the first and second powers.

Example 44 includes the subject matter of any one of Examples 28-43, and optionally, wherein the mobile device is configured to determine a pupillary distance between the lens and an other lens of the eyeglasses based on a distance between a first center of the lens and a second center of the other lens.

Example 45 includes the subject matter of Example 44, and optionally, wherein the mobile device is configured to process a first image of the object, which is captured without the lens; identify a second image captured via the lens, which co-aligns with the first image; determine a first location when the second image is captured; identify a third image captured via the other lens, which co-aligns with the first image; determine a second location when the third image is captured; and determine the pupillary distance based on the first and second locations.

Example 46 includes the subject matter of any one of Examples 28-45, and optionally, wherein the mobile device is configured to determine a sign of the lens based on the at least one image.

Example 47 includes the subject matter of Example 46, and optionally, wherein the mobile device is configured to identify a movement pattern in a plurality of captured images, the plurality of captured images comprising images of the object captured via the lens when the lens is moved in a particular direction, and to determine the sign of the lens based on the movement pattern.

Example 48 includes the subject matter of any one of Examples 28-47, and optionally, wherein the mobile device is configured to determine the one or more optical parameters of the lens based on a single frame including the at least one image of the object via the lens.

Example 49 includes the subject matter of any one of Examples 28-48, and optionally, wherein the one or more optical parameters of the lens comprise one or more parameters selected form the group consisting of a spherical power, a cylindrical power, a cylindrical axis, and a pupillary distance between lenses of the eyeglasses.

Example 50 includes the subject matter of any one of Examples 28-49, and optionally, wherein the mobile device is configured to cause a display device to display the object.

Example 51 includes the subject matter of Example 50, and optionally, wherein the mobile device is configured to calibrate a display size of the object on the display device.

Example 52 includes the subject matter of any one of Examples 28-51, and optionally, wherein the object comprises an object having one or more known dimensions, the mobile device configured to determine the optical parameters based on the dimensions.

Example 53 includes the subject matter of any one of Examples 28-52, and optionally, wherein the object comprises a circularly symmetric or rotationally symmetric object.

Example 54 includes the subject matter of any one of Examples 28-53, and optionally, wherein the mobile device is configured to cause the camera to capture the image of the object.

Example 55 includes a method of determining one or more optical parameters of a lens of eyeglasses, the method comprising processing at least one image of an object captured via the lens; and determining the one or more optical parameters of the lens based on the at least one image.

Example 56 includes the subject matter of Example 55, and optionally, comprising determining a power of the lens based on autofocus information of an image-capturing device, when the image is captured.

Example 57 includes the subject matter of Example 56, and optionally, comprising processing a first image of the object captured via the lens at a first distance between the object and the image-capturing device, and a second image of the object captured without the lens at a second distance between the object and the image-capturing device, and determining the power of the lens based on the first and second distances, first autofocus information of the image-capturing device when the first image is captured, and second autofocus information of the image-capturing device when the second image is captured.

Example 58 includes the subject matter of any one of Examples 55-57, and optionally, comprising determining a power of the lens based on a sharpness parameter of a sharpness of one or more spatial frequencies in the image.

Example 59 includes the subject matter of Example 58, and optionally, comprising processing a plurality of images of the object captured not via the lens at a respective plurality of distances between the object and an image-capturing device, determining a sharpest image of the plurality of images comprising the one or more spatial frequencies, and determining the power of the lens based on a first distance between the object and the image-capturing device, when the sharpest image is captured and a second distance between the object and the image-capturing device, when the at least one image is captured via the lens.

Example 60 includes the subject matter of any one of Examples 55-59, and optionally, comprising determining the one or more optical parameters of the lens based at least on one or more dimensions of the object.

Example 61 includes the subject matter of Example 60, and optionally, comprising determining one or more imaged dimensions of the object in the image, and determining the one or more optical parameters of the lens based at least on a magnification between the one or more dimensions and the one or more imaged dimensions.

Example 62 includes the subject matter of any one of Examples 55-61, and optionally, comprising identifying an existence of a cylindrical axis of the lens based on one or more visual affects of one or more spatial frequencies in the image.

Example 63 includes the subject matter of Example 62, and optionally, comprising determining the cylindrical axis based at least on an angle of a non-symmetrical blur of the one or more spatial frequencies.

Example 64 includes the subject matter of Example 62 or 63, and optionally, comprising determining existence of the cylindrical axis based at least on an angle of a sharpest portion of the spatial frequencies.

Example 65 includes the subject matter of any one of Examples 55-64, and optionally, comprising determining a cylindrical axis of the lens based on a comparison between one or more spatial elements of the object and one or more imaged spatial elements in the image.

Example 66 includes the subject matter of Example 65, and optionally, comprising processing a plurality of images corresponding to a plurality of rotations of the spatial elements in a plurality of angles, determining a plurality of magnifications between the one or more spatial elements of the object and the one or more imaged spatial elements, and determining the cylindrical axis based on the magnifications.

Example 67 includes the subject matter of any one of Examples 55-66, and optionally, comprising determining the one or more optical parameters of the lens based on a distance between the object and an image-capturing device, when the image is captured.

Example 68 includes the subject matter of Example 67, and optionally, comprising determining the distance between the object and the image-capturing device, based on acceleration information indicating an acceleration of the image capturing device.

Example 69 includes the subject matter of any one of Examples 55-68, and optionally, comprising determining a cylindrical power of the lens based on a cylindrical axis of the lens.

Example 70 includes the subject matter of Example 69, and optionally, comprising determining a first power of the lens at the cylindrical axis, determining a second power of the lens at a perpendicular axis, which is perpendicular to the cylindrical axis, and determining the cylindrical power based on the first and second powers.

Example 71 includes the subject matter of any one of Examples 55-70, and optionally, comprising determining a pupillary distance between the lens and an other lens of the eyeglasses based on a distance between a first center of the lens and a second center of the other lens.

Example 72 includes the subject matter of Example 71, and optionally, comprising processing a first image of the object, which is captured without the lens; identifying a second image captured via the lens, which co-aligns with the first image; determining a first location when the second image is captured; identifying a third image captured via the other lens, which co-aligns with the first image; determining a second location when the third image is captured; and determining the pupillary distance based on the first and second locations.

Example 73 includes the subject matter of any one of Examples 55-72, and optionally, comprising determining a sign of the lens based on the at least one image.

Example 74 includes the subject matter of Example 73, and optionally, comprising identifying a movement pattern in a plurality of captured images, the plurality of captured images comprising images of the object captured via the lens when the lens is moved in a particular direction, and determining the sign of the lens based on the movement pattern.

Example 75 includes the subject matter of any one of Examples 55-74, and optionally, comprising determining the one or more optical parameters of the lens based on a single frame including the at least one image of the object via the lens.

Example 76 includes the subject matter of any one of Examples 55-75, and optionally, wherein the one or more optical parameters of the lens comprise one or more parameters selected form the group consisting of a spherical power, a cylindrical power, a cylindrical axis, and a pupillary distance between lenses of the eyeglasses.

Example 77 includes the subject matter of any one of Examples 55-76, and optionally, comprising causing a display device to display the object.

Example 78 includes the subject matter of Example 77, and optionally, comprising calibrating a display size of the object on the display device.

Example 79 includes the subject matter of any one of Examples 55-78, and optionally, wherein the object comprises an object having one or more known dimensions, the method comprising determining the optical parameters based on the dimensions.

Example 80 includes the subject matter of any one of Examples 55-79, and optionally, wherein the object comprises a circularly symmetric or rotationally symmetric object.

Example 81 includes the subject matter of any one of Examples 55-80, and optionally, comprising causing an image capturing device to capture the image of the object.

Example 82 includes an apparatus to determine one or more optical parameters of a lens of eyeglasses, the apparatus comprising means for processing at least one image of an object captured via the lens; and means for determining the one or more optical parameters of the lens based on the at least one image.

Example 83 includes the subject matter of Example 82, and optionally, comprising means for determining a power of the lens based on autofocus information of an image-capturing device, when the image is captured.

Example 84 includes the subject matter of Example 83, and optionally, comprising means for processing a first image of the object captured via the lens at a first distance between the object and the image-capturing device, and a second image of the object captured without the lens at a second distance between the object and the image-capturing device, and determining the power of the lens based on the first and second distances, first autofocus information of the image-capturing device when the first image is captured, and second autofocus information of the image-capturing device when the second image is captured.

Example 85 includes the subject matter of any one of Examples 82-84, and optionally, comprising means for determining a power of the lens based on a sharpness parameter of a sharpness of one or more spatial frequencies in the image.

Example 86 includes the subject matter of Example 85, and optionally, comprising means for processing a plurality of images of the object captured not via the lens at a respective plurality of distances between the object and an image-capturing device, determining a sharpest image of the plurality of images comprising the one or more spatial frequencies, and determining the power of the lens based on a first distance between the object and the image-capturing device, when the sharpest image is captured and a second distance between the object and the image-capturing device, when the at least one image is captured via the lens.

Example 87 includes the subject matter of any one of Examples 82-86, and optionally, comprising means for determining the one or more optical parameters of the lens based at least on one or more dimensions of the object.

Example 88 includes the subject matter of Example 87, and optionally, comprising means for determining one or more imaged dimensions of the object in the image, and determining the one or more optical parameters of the lens based at least on a magnification between the one or more dimensions and the one or more imaged dimensions.

Example 89 includes the subject matter of any one of Examples 82-88, and optionally, comprising means for identifying an existence of a cylindrical axis of the lens based on one or more visual affects of one or more spatial frequencies in the image.

Example 90 includes the subject matter of Example 89, and optionally, comprising means for determining the cylindrical axis based at least on an angle of a non-symmetrical blur of the one or more spatial frequencies.

Example 91 includes the subject matter of Example 89 or 90, and optionally, comprising means for determining existence of the cylindrical axis based at least on an angle of a sharpest portion of the spatial frequencies.

Example 92 includes the subject matter of any one of Examples 82-91, and optionally, comprising means for determining a cylindrical axis of the lens based on a comparison between one or more spatial elements of the object and one or more imaged spatial elements in the image.

Example 93 includes the subject matter of Example 92, and optionally, comprising means for processing a plurality of images corresponding to a plurality of rotations of the spatial elements in a plurality of angles, determining a plurality of magnifications between the one or more spatial elements of the object and the one or more imaged spatial elements, and determining the cylindrical axis based on the magnifications.

Example 94 includes the subject matter of any one of Examples 82-93, and optionally, comprising means for determining the one or more optical parameters of the lens based on a distance between the object and an image-capturing device, when the image is captured.

Example 95 includes the subject matter of Example 94, and optionally, comprising means for determining the distance between the object and the image-capturing device, based on acceleration information indicating an acceleration of the image capturing device.

Example 96 includes the subject matter of any one of Examples 82-95, and optionally, comprising means for determining a cylindrical power of the lens based on a cylindrical axis of the lens.

Example 97 includes the subject matter of Example 96, and optionally, comprising means for determining a first power of the lens at the cylindrical axis, determining a second power of the lens at a perpendicular axis, which is perpendicular to the cylindrical axis, and determining the cylindrical power based on the first and second powers.

Example 98 includes the subject matter of any one of Examples 82-97, and optionally, comprising means for determining a pupillary distance between the lens and an other lens of the eyeglasses based on a distance between a first center of the lens and a second center of the other lens.

Example 99 includes the subject matter of Example 98, and optionally, comprising means for processing a first image of the object, which is captured without the lens; means for identifying a second image captured via the lens, which co-aligns with the first image; means for determining a first location when the second image is captured; means for identifying a third image captured via the other lens, which co-aligns with the first image; means for determining a second location when the third image is captured; and means for determining the pupillary distance based on the first and second locations.

Example 100 includes the subject matter of any one of Examples 82-99, and optionally, comprising means for determining a sign of the lens based on the at least one image.

Example 101 includes the subject matter of Example 100, and optionally, comprising means for identifying a movement pattern in a plurality of captured images, the plurality of captured images comprising images of the object captured via the lens when the lens is moved in a particular direction, and determining the sign of the lens based on the movement pattern.

Example 102 includes the subject matter of any one of Examples 82-101, and optionally, comprising means for determining the one or more optical parameters of the lens based on a single frame including the at least one image of the object via the lens.

Example 103 includes the subject matter of any one of Examples 82-102, and optionally, wherein the one or more optical parameters of the lens comprise one or more parameters selected form the group consisting of a spherical power, a cylindrical power, a cylindrical axis, and a pupillary distance between lenses of the eyeglasses.

Example 104 includes the subject matter of any one of Examples 82-103, and optionally, comprising means for causing a display device to display the object.

Example 105 includes the subject matter of Example 104, and optionally, comprising means for calibrating a display size of the object on the display device.

Example 106 includes the subject matter of any one of Examples 82-105, and optionally, wherein the object comprises an object having one or more known dimensions, the apparatus comprising means for determining the optical parameters based on the dimensions.

Example 107 includes the subject matter of any one of Examples 82-106, and optionally, wherein the object comprises a circularly symmetric or rotationally symmetric object.

Example 108 includes the subject matter of any one of Examples 82-107, and optionally, comprising means for causing an image capturing device to capture the image of the object.

Functions, operations, components and/or features described herein with reference to one or more embodiments, may be combined with, or may be utilized in combination with, one or more other functions, operations, components and/or features described herein with reference to one or more other embodiments, or vice versa.

While certain features have been illustrated and described herein, many modifications, substitutions, changes, and equivalents may occur to those skilled in the art. It is, therefore, to be understood that the appended claims are intended to cover all such modifications and changes as fall within the true spirit of the disclosure.

What is claimed is:

1. A product comprising one or more tangible computer-readable non-transitory storage media comprising computer-executable instructions operable to, when executed by at least one computer processor, enable the at least one computer processor to cause a computing device to:
   process an image of an object captured by an image-capturing device via a lens of eyeglasses when said lens is on an optical path extending between the image-capturing device and the object;
   determine an estimated distance, the estimated distance is between the object and the image-capturing device on the optical path when the image of the object is captured by the image-capturing device;
   determine a calculated magnification of the lens based on a dimension of the object and an imaged dimension of the object in the image;
   determine one or more optical parameters of said lens based on said estimated distance and said calculated magnification of the lens; and
   provide an output based on the one or more optical parameters of said lens.

2. The product of claim 1, wherein the instructions, when executed, cause the computing device to process an image of a graphical display comprising a first object and a second object, the image of the graphical display comprising a first image of the first object captured by the image-capturing device via the lens, and a second image of the second object captured by the image-capturing device not via the lens, and wherein the instructions, when executed, cause the computing device to determine the calculated magnification based on a dimension of the first object and an imaged dimension of the first object in the first image, and to determine the estimated distance by determining an estimated distance between the image-capturing device and the graphical display in the optical path based on the second image of the second object.

3. The product of claim 1, wherein the instructions, when executed, cause the computing device to determine the estimated distance between the object and the image-capturing device based on a predefined object in the image captured by the image-capturing device.

4. The product of claim 1, wherein the instructions, when executed, cause the computing device to identify an existence of a cylindrical axis of the lens based on the image, to determine a first power of the lens corresponding to said cylindrical axis based on the calculated magnification, to determine a second power of said lens corresponding to a perpendicular axis, which is perpendicular to said cylindrical axis, and to determine a cylindrical power of said lens based on said first and second powers.

5. The product of claim 4, wherein the instructions, when executed, cause the computing device to determine a spherical power of the lens based on the first power.

6. The product of claim 4, wherein the imaged dimension of the object in the image comprises an imaged dimension of an element of the object corresponding to the cylindrical axis.

7. The product of claim 1, wherein the instructions, when executed, cause the computing device to determine a power of the lens based on autofocus information of the image-capturing device, when said image is captured.

8. The product of claim 7, wherein the instructions, when executed, cause the computing device to process a first image of said object captured via said lens at a first distance between said object and said image-capturing device, and a second image of said object captured without said lens at a second distance between said object and said image-capturing device, and to determine the power of the lens based on said first and second distances, first autofocus information of said image-capturing device when said first image is captured, and second autofocus information of said image-capturing device when said second image is captured.

9. The product of claim 1, wherein the instructions, when executed, cause the computing device to determine a power of the lens based on a sharpness parameter of a sharpness of one or more spatial frequencies in said image.

10. The product of claim 9, wherein the instructions, when executed, cause the computing device to process a plurality of images of said object captured not via said lens at a respective plurality of distances between said object and the image-capturing device, to determine a sharpest image of said plurality of images comprising the one or more spatial frequencies, and to determine the power of the lens based on a first distance between said object and said image-capturing device, when said sharpest image is captured and a second distance between said object and said image-capturing device, when said at least one image is captured via said lens.

11. The product of claim 1, wherein the instructions, when executed, cause the computing device to identify an existence of a cylindrical axis of the lens based on one or more visual affects of one or more spatial frequencies in said image.

12. The product of claim 11, wherein the instructions, when executed, cause the computing device to determine said cylindrical axis based at least on an angle of a non-symmetrical blur of said one or more spatial frequencies.

13. The product of claim 11, wherein the instructions, when executed, cause the computing device to determine existence of said cylindrical axis based at least on an angle of a sharpest portion of said spatial frequencies.

14. The product of claim 1, wherein the instructions, when executed, cause the computing device to determine a cylindrical axis of said lens based on a comparison between one or more spatial elements of said object and one or more imaged spatial elements in said image.

15. The product of claim 14, wherein the instructions, when executed, cause the computing device to process a plurality of images corresponding to a plurality of rotations of said spatial dements in a plurality of angles, to determine a plurality of magnifications between said one or more spatial elements of said object and said one or more imaged spatial elements, and to determine said cylindrical axis based on said magnifications.

16. The product of claim 1, wherein the instructions, when executed, cause the computing device to determine the one or more optical parameters of said lens based on an estimated distance between said lens and the image-capturing device, when said image is captured.

17. The product of claim 1, wherein the instructions, when executed, cause the computing device to determine the estimated distance between said object and said image-capturing device, based on acceleration information indicating an acceleration of said image-capturing device.

18. The product of claim 1, wherein the instructions, when executed, cause the computing device to determine a cylindrical power of said lens based on a cylindrical axis of said lens.

19. The product of claim 1, wherein the instructions, when executed, cause the computing device to determine a pupillary distance between said lens and an other lens of said eyeglasses based at least on the captured image.

20. The product of claim 1, wherein the instructions, when executed, cause the computing device to determine a sign of said lens based at least on said captured image.

21. The product of claim 20, wherein the instructions, when executed, cause the computing device to identify a movement pattern in a plurality of captured images, the plurality of captured images comprising images of said object captured via said lens during relative movement between the lens and the image capturing device in a particular direction, and to determine the sign of said lens based on said movement pattern.

22. The product of claim 1, wherein the instructions, when executed, cause the computing device to determine the one or more optical parameters of said lens based on a single frame captured by the image-capturing device, the single frame including said image of said object via said lens.

23. The product of claim 1, wherein the one or more optical parameters of said lens comprise one or more parameters selected foimi the group consisting of a spherical power, a cylindrical power, a cylindrical axis, and a pupillary distance between lenses of said eyeglasses.

24. The product of claim 1, wherein the instructions, when executed, cause the computing device to cause a display device to display said object.

25. The product of claim 1, wherein the object comprises a circularly symmetric or rotationally symmetric object.

26. The product of claim 1, wherein the instructions, when executed, cause the computing device to cause the image-capturing device to capture the image of said object.

27. An apparatus comprising:
an image-capturing device to capture an image of an object via a lens of eyeglasses when said lens is on an optical path between the image-capturing device and the object; and
a processor configured to provide an output based on one or more optical parameters of said lens by:
determining an estimated distance, the estimated distance i-s-being on the optical path between the object and the image-capturing device when the image of the object is captured by the image-capturing device;
determining a calculated magnification of the lens based on a dimension of the object and an imaged dimension of the object in the image; and
determining the one or more optical parameters of said lens based on said estimated distance and said calculated magnification of the lens.

28. The apparatus of claim 27, wherein the processor is configured to process an image of a graphical display comprising a first object and a second object, the image of the graphical display comprising a first image of the first object captured by the image-capturing device via the lens, and a second image of the second object captured by the image-capturing device not via the lens, and wherein the processor is configured to determine the calculated magnification based on a dimension of the first object and an imaged dimension of the first object in the first image, and to determine the estimated distance by determining an estimated distance between the image-capturing device and the graphical display based on the second image of the second object.

29. The apparatus of claim 27, wherein the processor is configured to determine the one or more optical parameters of said lens based on an estimated distance between said lens and the image-capturing device, when said image is captured.

30. An apparatus comprising:
a computing device including a processor and an electronic storage medium, the medium storing electronic instructions that, when executed by the processor, cause the processor to:
process an image of an object captured by an image-capturing device via a lens of eyeglasses when said lens is on an optical path extending between the image-capturing device and the object;
determine an estimated distance, the estimated distance is between the object and the image-capturing device when the image of the object is captured by the image-capturing device;
determine a calculated magnification of the lens based on a dimension of the object and an imaged dimension of the object in the image;
determine one or more optical parameters of said lens based on said estimated distance and said calculated magnification of the lens; and
provide an output based on the one or more optical parameters of said lens.

31. The apparatus of claim 30, wherein the instructions further cause the processor to process an image of a graphical display comprising a first object and a second object, the image of the graphical display comprising a first image of the first object captured by the image-capturing device via the lens, and a second image of the second object captured by the image-capturing device not via the lens, and wherein the instructions further cause the processor to determine the calculated magnification based on a dimension of the first object and an imaged dimension of the first object in the first image, and determine the estimated distance by determining an estimated distance between the image-capturing device and the graphical display based on the second image of the second object.

* * * * *